(12) United States Patent
Popescu et al.

(10) Patent No.: US 8,520,213 B2
(45) Date of Patent: Aug. 27, 2013

(54) SPATIAL LIGHT INTERFERENCE MICROSCOPY AND FOURIER TRANSFORM LIGHT SCATTERING FOR CELL AND TISSUE CHARACTERIZATION

(75) Inventors: Gabriel Popescu, Champaign, IL (US); Huafeng Ding, Urbana, IL (US); Zhuo Wang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/342,350

(22) Filed: Jan. 3, 2012

(65) Prior Publication Data

US 2012/0105858 A1  May 3, 2012

Related U.S. Application Data

(62) Division of application No. 12/454,660, filed on May 21, 2009, now Pat. No. 8,184,298.

(60) Provisional application No. 61/054,939, filed on May 21, 2008, provisional application No. 61/207,840, filed on Jan. 12, 2009.

(51) Int. Cl.
*G01B 9/02* (2006.01)
*G01J 3/45* (2006.01)

(52) U.S. Cl.
USPC .......................................................... 356/456

(58) Field of Classification Search
USPC .................. 356/451, 456, 521; 359/370
See application file for complete search history.

(56) References Cited

U.S. PATENT DOCUMENTS

| | | | | |
|---|---|---|---|---|
| 5,208,651 | A * | 5/1993 | Buican | 356/451 |
| 6,525,875 | B1 | 2/2003 | Lauer | 359/371 |
| 6,934,035 | B2 | 8/2005 | Yang et al. | 356/485 |
| 7,349,085 | B1 | 3/2008 | Tan et al. | 356/364 |
| 7,365,858 | B2 | 4/2008 | Fang-Yen et al. | 356/489 |
| 7,460,240 | B2 | 12/2008 | Akcakir | 356/457 |
| 2005/0105097 | A1 | 5/2005 | Fang-Yen et al. | 356/497 |
| 2009/0125242 | A1* | 5/2009 | Choi et al. | 702/19 |

OTHER PUBLICATIONS

Park, YongKeun et al. "Diffraction phase and fluorescence microscopy". Optics Express, vol. 14, No. 18, Sep. 4, 2006, pp. 8263-8268.*
Amin, M. Shahrooz et al. "Microrheology of red blood cell membranes using dynamic scattering microscopy". Optics Express, vol. 15, No. 25, Dec. 10, 2007, pp. 17001-17009.*

(Continued)

*Primary Examiner* — Michael A Lyons
(74) *Attorney, Agent, or Firm* — Lathrop & Gage LLP

(57) ABSTRACT

Methods and apparatus for rendering quantitative phase maps across and through transparent samples. A broadband source is employed in conjunction with an objective, Fourier optics, and a programmable two-dimensional phase modulator to obtain amplitude and phase information in an image plane. Methods, referred to as Fourier transform light scattering (FTLS), measure the angular scattering spectrum of the sample. FTLS combines optical microscopy and light scattering for studying inhomogeneous and dynamic media. FTLS relies on quantifying the optical phase and amplitude associated with a coherent image field and propagating it numerically to the scattering plane. Full angular information, limited only by the microscope objective, is obtained from extremely weak scatterers, such as a single micron-sized particle. A flow cytometer may employ FTLS sorting.

16 Claims, 26 Drawing Sheets
(9 of 26 Drawing Sheet(s) Filed in Color)

(56) References Cited

OTHER PUBLICATIONS

Popescu, Gabriel et al. "Imaging red blood cell dynamics by quantitative phase microscopy". Blood Cells, Molecules, and Diseases 41, Apr. 1, 2008, pp. 10-16.*

Ahn et al., "Harmonic phase-dispersion microscope with a Mach-Zehnder interferometer," *Applied Optics*, vol. 44, No. 7, pp. 1188-1190 (Mar. 2005).

Amin et al., "Microrheology of red blood cell membranes using dynamic scattering microscopy," *Optics Express*, vol. 15, No. 25, pp. 17001-17009 (Dec. 2007).

Bizheva et al., "Path-length-resolved dynamic light scattering in highly scattering random media: The transition to diffusing wave spectroscopy," *Physical Review E*, vol. 58, No. 6, pp. 7664-7667 (Dec. 1998).

Ding et al. "Optical properties of tissues quantified by Fourier-transform light scattering," *Optics Letters*, vol. 34, No. 9, pp. 1372-1374 (May 2009).

Hillman et al. "Microscopic particle discrimination using spatially-resolved Fourier-holographic light scattering angular spectroscopy," *Optics Express*, vol. 14, No. 23, pp. 11088-11102 (Nov. 2006).

Ikeda et al. "Hilbert phase microscopy for investigating fast dynamics in transparent systems," *Optics Letters*, vol. 30, No. 10, pp. 1165-1167 (May 2005).

Lue et al. "Quantitative phase imaging of live cells using fast Fourier phase microscopy," *Applied Optics*, vol. 46, No. 10, pp. 1836-1842 (Apr. 2007).

Popescu et al. "Fourier phase microscopy for investigation of biological structures and dynamics," *Optics Letters*, vol. 29, No. 21, pp. 2503-2505 (Nov. 2004).

Popescu et al. "Erythrocyte structure and dynamics quantified by Hilbert phase microscopy," *Journal of Biomedical Optics*, vol. 10, No. 6, pp. 060503-1-060503-3 (Nov./Dec. 2005).

Popescu et al. "Diffraction phase microscopy for quantifying cell structure and dynamics," *Optics Letters*, vol. 31, No. 6, pp. 775-777 (Mar. 2006).

Popescu "Quantitative phase imaging and applications: a review," pp. 1-32 (Oct. 2006), [retrieved on May 2, 2008], Retrieved from the Internet: < URL: http://light.ece.uiue.edu/QPI_review.htm>.

Wilson et al. "Mie theory interpretations of light scattering from intact cells," *Optics Letters*, vol. 30, No. 18, pp. 2442-2444 (Sep. 2005).

* cited by examiner

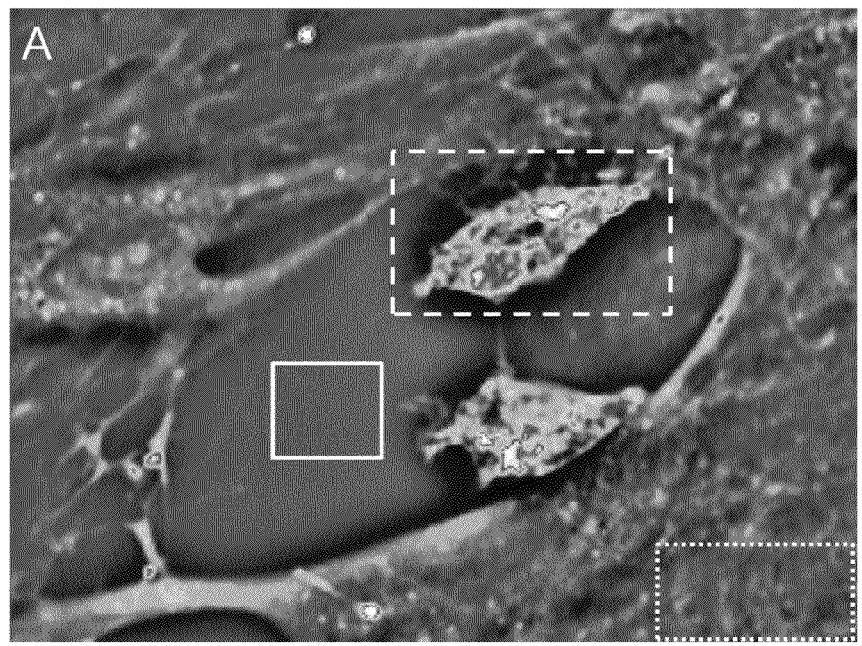
FIG. 12a
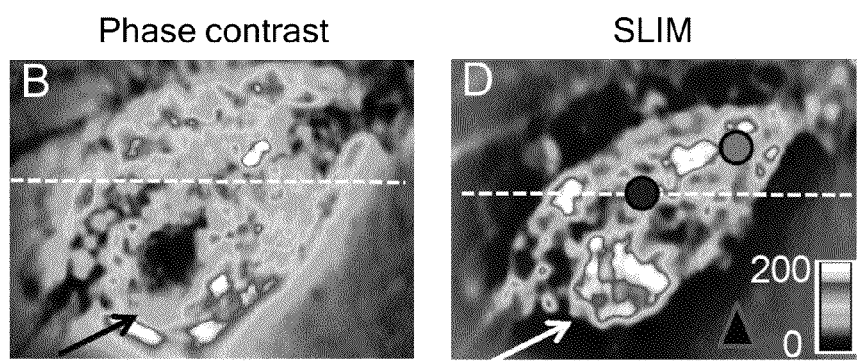
FIG. 12b
FIG. 12d
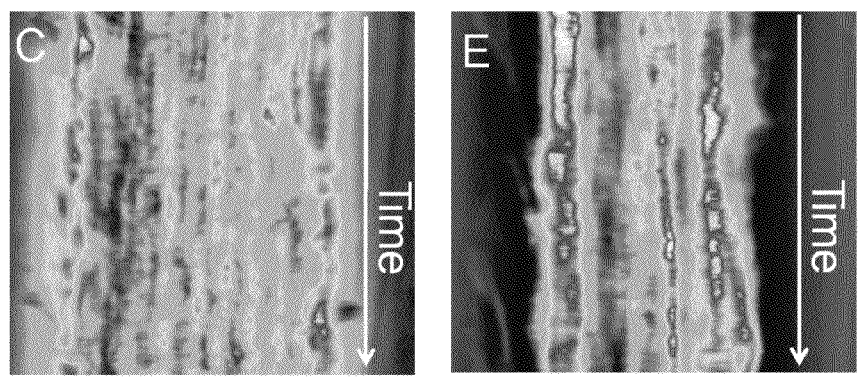
FIG. 12c
FIG. 12e

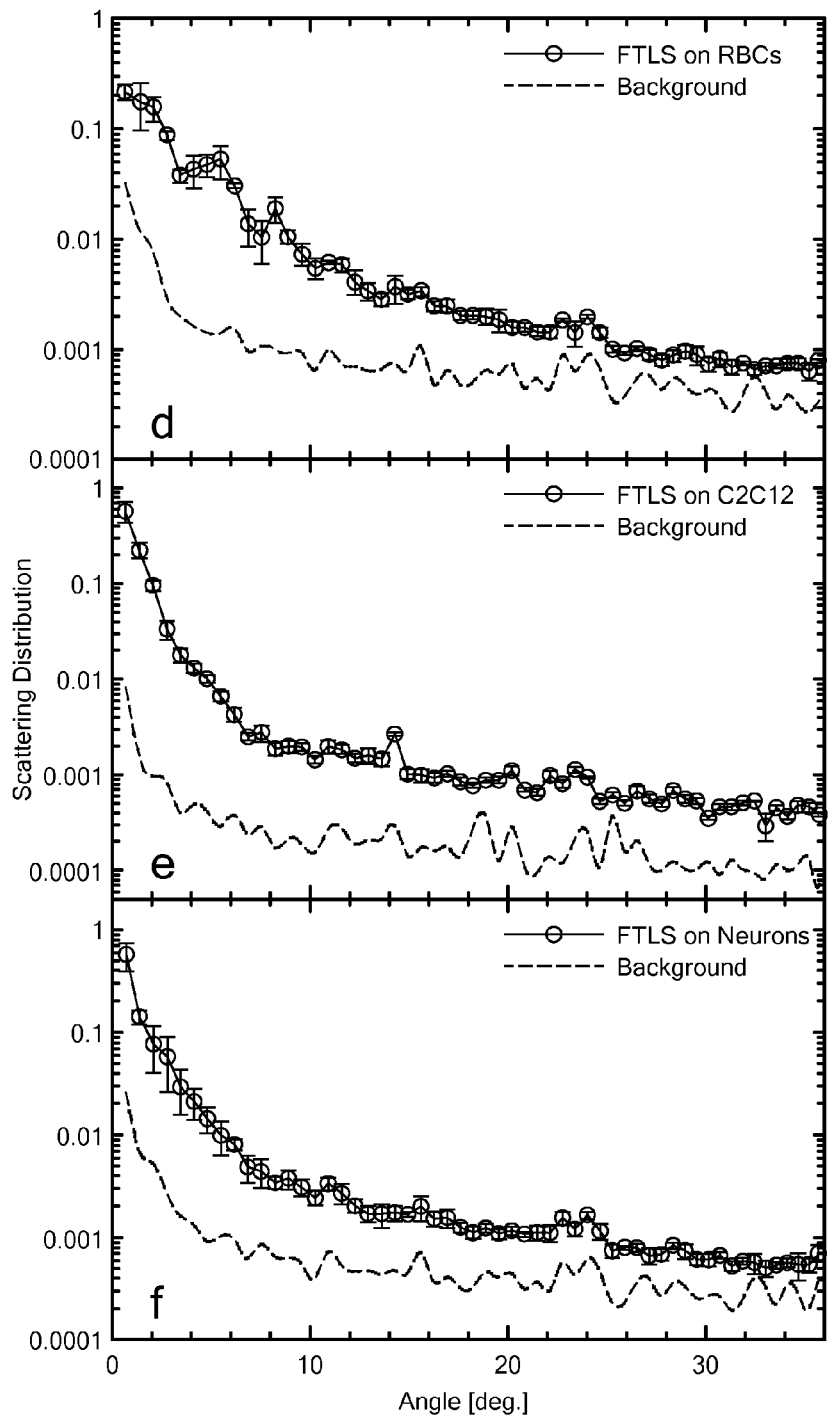

SPATIAL LIGHT INTERFERENCE MICROSCOPY AND FOURIER TRANSFORM LIGHT SCATTERING FOR CELL AND TISSUE CHARACTERIZATION

The present application is a divisional application of co-pending U.S. patent application Ser. No. 12/454,660, filed May 21, 2009, and, like that application, claims the priority of U.S. Provisional Patent Application, Ser. No. 61/054,939, filed May 21, 2008, and U.S. Provisional Patent Application, Ser. No. 61/204,840, filed Jan. 12, 2009, all of which applications are incorporated by reference herein.

The present invention was developed with Government support under NIH Grants HL086870 and HD007333, and under CAREER Award Grant 08-46660 awarded by the National Science Foundation. The Government has certain rights in the invention.

TECHNICAL FIELD

The present invention pertains to apparatus and methods for quantitative imaging of the optical phase shift introduced by largely transparent samples, and for analyzing angular scattering over a broad range of angles by a sample that may include single particles and live cells, and, further, to the application of the foregoing apparatus and methods for characterizing cells and tissue.

BACKGROUND OF THE INVENTION

For centuries, light microscopy has been the main tool for studying cells under physiological conditions. In the 19$^{th}$ century, Ernst Abbe formulated the resolution limitation of the light microscope as approximately half the light wavelength, or 200-300 nanometers. Abbe's theory is discussed in detail in Born & Wolf, *Principles of Optics* (7$^{th}$ ed.) (1999), incorporated herein by reference, at pp. 467 ff. Electron microscopy (EM), on the other hand, can reveal nanometer scale details of the cellular structure because the wavelength associated with an accelerated electron is correspondingly smaller than that of a visible photon. However, EM has inherent limitations due to the heavy sample preparation involved, which prohibits investigating cells non-invasively. Many outstanding questions in cell biology could be answered if light microscopy provided the nanometer level resolution afforded by electron microscopy.

In recent years, several approaches have been developed to surmount the diffraction barrier in fluorescence microscopy, thereby representing a paradigm shift from the resolution limit formulated by Abbe. However, the current applications of these techniques are, in many cases, limited by specific technological constraints. First, in all approaches, the fluorescent light detected is very weak, which demands a correspondingly long exposure time, itself limited by photobleaching. Second, saturation techniques, such as stimulated emission depletion and structured illumination require a high level of excitation power to be delivered to the sample, which raises the issue of photo-damage and ultimately limits the safe exposure time. Third, approaches based on stochastic photo-switchable dyes operate based on the prior assumption of a sparse distribution of fluorescent molecules, which limits applications to dynamic imaging and long-time investigation.

The foregoing limitations may be overcome if the nanoscale cell structure and dynamics information is accessed via intrinsic contrast, i.e., without exogenous agents, such as fluorescent dyes. The great obstacle in this case becomes the fact that, generally, cells of single- and multi-cellular organisms do not absorb or scatter light significantly, i.e., they are essentially transparent, or phase objects. The phase contrast (PC) method of Zernike, *Science* 121, p. 345 (1955), which is incorporated herein by reference, represented a major advance in intrinsic contrast imaging, as it revealed inner details of transparent structures without staining or tagging. In PC, a phase shift of $\pi/2$ is introduced between the scattered and unscattered light, which makes the two interfere with greater contrast at the image plane. While PC is sensitive to minute optical path changes in the cell, down to the nanoscale, the information retrieved is qualitative, i.e., it does not provide the actual phase delay through the sample.

The intensity of light scattered by a particle as a function of the angle between the incident illumination and the scattered wave, and, more particularly, as a function of the incident wavelength and polarization, depends on the dimensions, morphology, optical susceptibility (or refractive index) and orientation of the scattering particle.

Elastic (static) light scattering (ELS) has made a broad impact in understanding inhomogeneous matter, from atmosphere and colloidal suspensions to rough surfaces and biological tissues. In ELS, by measuring the angular distribution of the scattered field, one can infer noninvasively quantitative information about the sample structure (i.e. its spatial distribution of refractive index). Dynamic (quasi-elastic) light scattering (DLS) is the extension of ELS to dynamic inhomogeneous systems. The temporal fluctuations of the optical field scattered at a particular angle by an ensemble of particles under Brownian motion relates to the diffusion coefficient of the particles. Diffusing wave spectroscopy integrates the principle of DLS in highly scattering media. More recently, dynamic scattering from a probe particle has been used to study the mechanical properties of the surrounding complex fluid of interest. Thus, microrheology, in which viscoelastic information is retrieved over various temporal and length scales, remains a subject of intense current research especially in the context of cell mechanics.

Light scattering techniques have the benefit of providing information that is intrinsically averaged over the measurement volume. However, it is often the case that the spatial resolution achieved is insufficient. "Particle tracking" microrheology alleviates this problem by measuring the particle displacements in the imaging (rather than scattering) plane. However, the drawback in the case of particle tracking is that relatively large particles are needed such that they can be tracked individually, which also limits the throughput required for significant statistical average.

The use of angular light scattering (ALS) or light scattering spectroscopy (LSS), generally, as techniques for studying the features of individual particles, and of particles in the aggregate, has a long history. Recent application to intact cells is the subject of Wilson et al., *Mie theory interpretations of light scattering from intact cells, Opt. Lett.*, vol. 30, pp. 2442-44 (2005), while coherent techniques, using reference beams of varying degrees of coherence, have been applied to ALS, as described, for example, in Hillman, et al., *Microscopic particle discrimination using spatially-resolved Fourier-holographic light scattering angular spectroscopy, Opt. Express*, vol. 14, pp. 11088-11102 (2006), both of which references are incorporated herein by reference. All prior art coherent light scattering measurements have entailed measurements in the Fourier plane, such that each angle must be detected separately, by a distinct detector element or set of detector elements.

SUMMARY OF THE INVENTION

In accordance with preferred embodiments of the present invention, methods are provided for determining an angular scattering distribution, in a scattering plane, of a sample containing at least one particle. These methods have steps of:

a. illuminating the sample with light;

b. combining, at a detector array disposed at an image plane, a first instance of the light, the first instance substantially devoid of spatial frequency information due to the sample, with a second instance of the light, the second instance containing spatial frequency information due to scattering by the sample, such as to produce an interference signal;

c. numerically propagating a pattern associated with the interference signal at the image plane to obtain the angular scattering distribution in the scattering plane; and d. providing a tangible image of the angular scattering distribution in the scattering plane.

In accordance with other embodiments of the invention, the interference signal may be spatially high-pass filtered to obtain an interferogram based on a cross-term of the first and second instances of the monochromatic light. The first instance of light may not traverse the sample, or else, both the first and second instances of the light may both traverse the sample and may be split, into a zeroeth order and at least one higher order, with respect to one another by a diffractive element disposed substantially in an image plane. In that case, the first instance of the light may be derived from the zeroeth order of the diffractive element. The first instance of the light may also be low-pass filtered in a Fourier plane of a spatial filtering lens system.

In further embodiments of the invention, the angular scattering distribution may be separated into a form field characterizing a single particle and a structural field describing spatial correlations in particle positions. The steps of obtaining images may be repeated in order to obtain a set of dynamic light scattering signals, as well as a power spectrum of the set of dynamic light scattering signals.

In accordance with another aspect of the present invention, a flow cytometer is provided that has a flow cell for streaming biological cells within a fluid medium, a source of substantially spatially coherent illumination for illuminating a subset of the biological cells within the flow cell, an objective for collecting light scattered by the illuminated subset of biological cells and for imaging the light in an imaging plane. A dispersing element diffracts light in an imaging plane into at least two diffraction orders, one order comprising a reference beam, with a spatial filtering lens system provided for removing any spatial structure due to the fluid medium from the reference beam. A detector array is used to create an interference signal based on combination of the two diffraction orders, with a processor transforming the interference signal to obtain an angular scattering distribution in a scattering plane associated with the illuminated subset of biological cells. This allows the cells to be characterized on the basis of angular scattering distribution.

In accordance with yet another aspect of the invention, an imaging phase quantification module is provided for use with a phase contrast microscope having a source of light for illuminating a specimen. The imaging phase quantification module has:

a. spatially Fourier transforming optics for transforming light transmitted through the specimen to create a spatially transformed image;

b. a modulator for spatially modulating at least one of the phase and amplitude of the spatial frequency components of the spatially transformed image;

c. a detector array for detecting an intensity image of the specimen plane as modulated with respect to spatial frequency components; and d. a processor for deconvolving the intensity image at a plurality of spatially modulated instances to obtain a three-dimensional phase representation of the specimen at each of a plurality of distances relative to a fiducial plane.

Another aspect of the present invention provides a method for deriving a quantitative phase contrast image of a specimen, wherein the method has steps of:

a. illuminating the specimen with illuminating light characterized by a coherence length substantially shorter than 10 micrometers;

b. scanning a focus to a plurality of depths plurality of depths within the specimen;

c. spatially Fourier transforming light transmitted through the specimen at each of the plurality of depths;

d. spatially modulating at least one of the phase and amplitude of the spatial frequency components of the spatially transformed image;

e. detecting an intensity image of the specimen plane as modulated with respect to spatial frequency components; and f. deconvolving the intensity image at a plurality of spatially modulated instances to obtain a three-dimensional phase representation of the specimen at each of the plurality of distances relative to a fiducial plane.

The illuminating light may be characterized by a coherence length no greater than about 10 microns, and by a coherence length no greater than about 1.5 microns. The illuminating light may be focused onto the specimen with an optic characterized by a numerical aperture exceeding 0.5. The specimen, more particularly, may be a substantially cylindrical object, such as a nanotube or neuron processor.

In accordance with a further aspect of the invention, an improvement to a phase contrast microscope is provided, where the phase contrast microscope is of the sort having a source of illumination and an optical system for directing the illumination via a fixed condenser aperture phase contrast mask to a specimen and collecting light transmitted therethrough. The improvement has optics for forming a spatial transform of the collected light in a transform plane, a modulator for modulating at least one of the phase and amplitude of light in the transform plane, a detector array for detecting the modulated light; and a processor for transforming an intensity image at a plurality of spatially modulated instances, to obtain a three-dimensional phase representation of the specimen. The plurality of spatially modulated instances may includes at least three distinct phase delays, which may be integral multiples of a specified phase shift at a central frequency defined with respect to a spectrum of the source of illumination. The modulator may be a two-dimensional phase modulator, or, more particularly, at least one of a liquid crystal spatial light modulator, a deformable mirror, and a micromirror array. The modulator may be a spatial light modulator employed in either reflection or transmission. In other embodiments, the modulator may be disposed within a microscope objective module.

In another aspect of the invention, a phase-modulating microscope objective is provided that has at least one objective lens, and, at the same time, a variable phase plate for modulating an optical depth traversed by light through each of a plurality of pixels.

Yet another aspect of the invention provides a method for optical sectioning through a specimen. This method has steps of:

a. employing an improved phase contrast microscope in accordance with the present invention;

b. transforming light transmitted through the live cell to create a spatially transformed image;

c. spatially modulating at least one of phase and amplitude of the spatial frequency components of the spatially transformed image;

d. detecting an intensity image of the specimen plane as modulated with respect to spatial frequency components; and e. transforming the intensity image at a plurality of spatially modulated instances to obtain a three-dimensional phase representation of the live cell at each of a plurality of distances relative to a fiducial plane.

The specimen may be a live cell, and nanoscale motions may be quantified without physical contact by recording changes in phase images as a function of time. In related methods, the changes in phase images may provide a measure of cell growth, and transforming light transmitted through a live cell may entail doing so non-invasively. Alternatively, the specimen may be a structure that includes at least one thin film.

BRIEF DESCRIPTION OF THE DRAWINGS

The present patent or application file contains at least one drawing executed in color. Copies of this patent or patent application publication with color drawing(s) will be provided by the Office upon request and payment of the necessary fee.

The foregoing features of the invention will be more readily understood by reference to the following detailed description, taken with reference to the accompanying drawings, in which:

FIG. 12A-12H demonstrate SLIM dynamic imaging of mixed glial-microglial cell culture. FIG. 12A is a phase map of two microglia cells active in a glia cell environment. The box outlined by a solid line box indicates the background used in G, dashed line box crops a reactive microglia cell used in B-E and dotted line box indicates glial cell membrane used in G and H. FIG. 12B is a phase contrast image of the cell shown in 12A. FIG. 12C is a registered time-lapse projection of the corresponding cross-section through the cell as indicated by the dash line in FIG. 12B. The signal represents intensity and has no quantitative meaning. FIG. 12D is a SLIM image of the cell in B; the fields of view are the same. The arrows in B and D point to the nucleus which is incorrectly displayed by PC as a region of low signal. FIG. 12E is a registered time-lapse projection of the corresponding cross-section through the cell as indicated by the dash line in D. The color bar indicates path-length in nm. FIG. 12F shows path-length fluctuations of the points on the cell (indicated in D) showing quasi-periodic intracellular motions (blue- and green-filled circles). Background fluctuations (black) are negligible compared to the active signals of the microglia. FIG. 12G is a semi-logarithmic plot of the optical path-length displacement distribution associated with the glial cell membrane indicated by the dotted box in A. The solid lines show fits with a Gaussian and exponential decay, as indicated in the legend. The distribution crosses over from a Gaussian to an exponential behavior at approximately 10 nm. The background path-length distribution, measured from the solid line box, has a negligible effect on the signals from cells and is fitted very well by a Gaussian function. The inset shows an instantaneous path-length displacement map associated with the membrane. FIG. 12H shows mean-squared displacements vs. spatial wave vector for 6 different membrane patches and their average (solid curve). At large q vectors the $q^{-2}$ indicates membrane tension.

FIGS. 15d-15f are scattering phase functions corresponding to FIGS. 15a-15c as measured by FTLS in accordance with an embodiment of the present invention.

DETAILED DESCRIPTION OF SPECIFIC EMBODIMENTS

In accordance with preferred embodiments of the present invention, the high spatial resolution associated with optical microscopy and the intrinsic averaging of light scattering techniques may be combined advantageously in methods referred to collectively as Fourier transform light scattering (FTLS) that may be employed for studying both static and dynamic light scattering.

General features of the present invention are now described with reference to FIG. 1, which depicts a Fourier light scattering apparatus, designated generally by numeral 10.

As will be described, FTLS provides for retrieving the phase and amplitude associated with a coherent microscope image and numerically propagating this field to the scattering plane. This approach may advantageously provide both the accurate phase retrieval for the ELS measurements and, further, the fast acquisition speed required for DLS studies.

Figure 1:
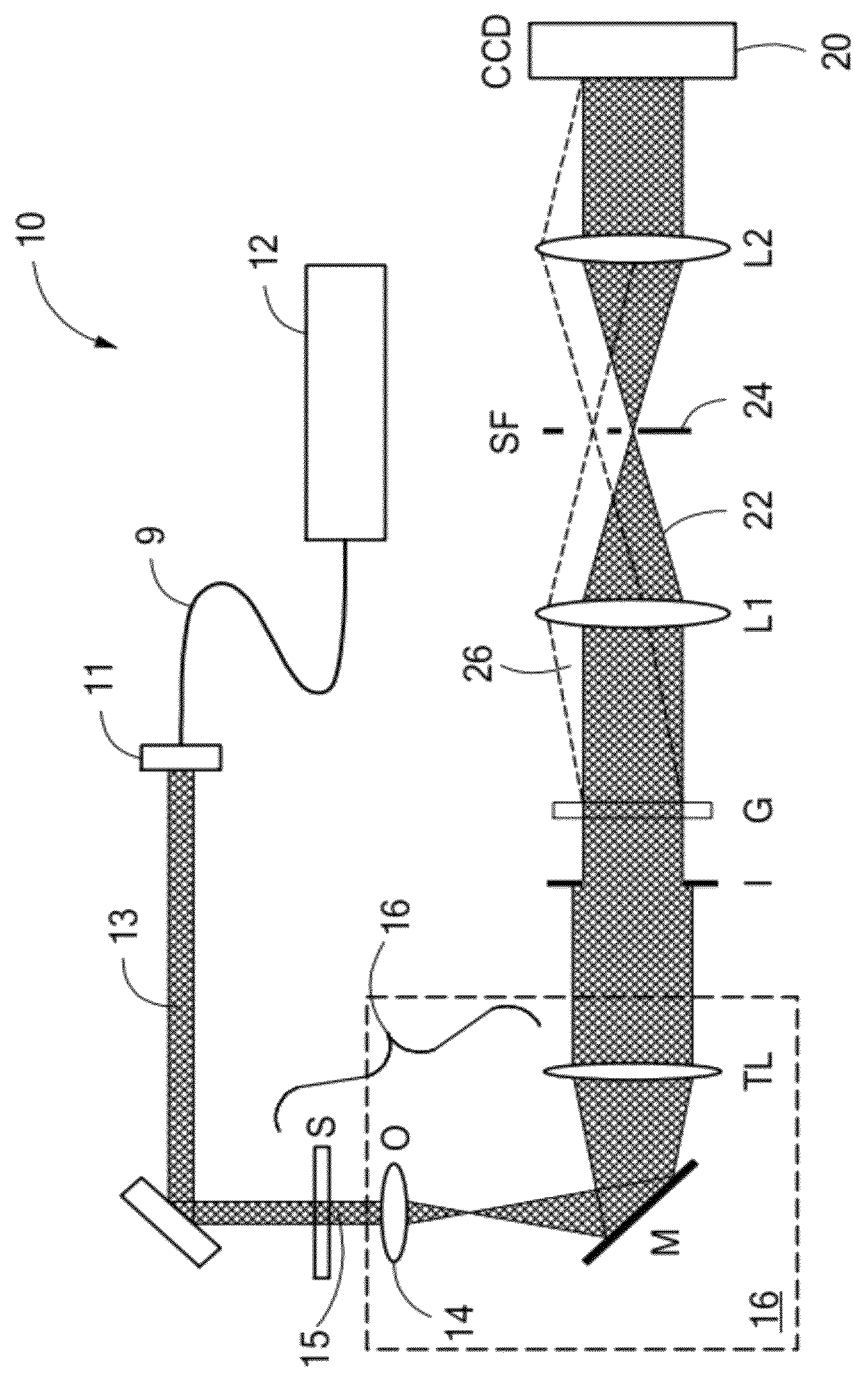
FIG. 1 is a schematic depiction of an angular light scattering measurement apparatus in accordance with one embodiment of the present invention.

While the FTLS apparatus 10 is depicted in FIG. 1 in the form of a common-path interferometer, it is to be understood, however, that all other interferometric configurations are within the scope of the present invention. In particular, a further apparatus for phase imaging in accordance with the present invention, and referred to herein as "spatial light interference microscopy" ("SLIM") is described below, in reference to FIG. 6.

In the embodiment of FIG. 1, a source 12 of light characterized by a high degree of spatial coherence is used to illuminate a sample S (otherwise referred to, herein, and in appended claims, as a "specimen"). An exemplary source employs a doubled ($\lambda$=532 nm) diode-pumped Nd:YAG laser, although other sources may be used within the scope of the present invention. Light 13 emitted by source 12 is substantially monochromatic. An objective 14 collects the light transmitted through the sample. Sample S and objective 14 may be mounted on a commercial computer-controlled microscope 16, such as a Carl Zeiss Axio Observer Z1, for example. The term "microscope," as used herein and in any appended claims, is used, in a non-limiting sense, to refer to any optical configuration which magnifies an image of a sample.

To ensure substantially full spatial coherence, light beam 13 may be coupled into a single mode fiber 9 and further collimated by a fiber collimator 11. Typical beam size at the sample plane is larger than a centimeter, and typical total beam power is approximately 3 milliwatts. Light 15 scattered by the sample is collected by the objective lens 14 of the microscope, and is imaged at the side port of the microscope. While scattering in a general forward direction is depicted in FIG. 1, it is to be understood that scattered light may be collected, in accordance with the present invention, in other directions as well.

In order to obtain phase information with respect to scattered light 15, in accordance with preferred embodiments of the invention, scattered light is interfered with a reference beam derived from the same spatially coherent source 12 as the light illuminating the sample. The reference beam and the beam carrying scattering information may be referred to respectively, herein and in any appended claims, as a first and second instance of light 13 derived from coherent source 12. The reference beam is devoid of spatial frequency information due to the sample.

In one embodiment of the invention, the first and second instances of monochromatic light share a common path through the sample S. A diffractive element, such as diffraction grating G, with a typical pitch of 110 grooves/mm, is placed at an interim image plane I, thus generating multiple diffraction orders containing full spatial information about the image. While the diffractive element is depicted as a transmission grating, it is to be understood that other diffractive elements, such as a reflection grating, are also within the scope of the present invention. In order to establish a common-path Mach-Zender interferometer, a standard spatial filtering lens system $L_1$-$L_2$ is used to select the two diffraction orders and generate a final interferogram at CCD plane 20, which is an image plane. Typical focal lengths for $L_1$ and $L_2$ respectively are 60 mm and 300 mm. CCD plane 20 is where the interferogram is detected by a detector array, such as a charge-coupled device, designated in FIG. 1 as CCD. It is to be understood that the use of any other detector array technology is within the scope of the present invention.

The $0^{th}$ order beam 22 that is not diffracted by grating G is low-pass filtered using the spatial filter 24 (typically a pinhole of 25 µm diameter) positioned in the spatial filter plane SF, namely, the Fourier plane of $L_1$, such that at the CCD plane 20 it approaches a uniform field. Simultaneously, the spatial filter allows passing the entire frequency content of the $1^{st}$ diffraction order beam and blocks all the other orders. The 1st order 26 (shown between dashed lines) is thus the imaging field and the $0^{th}$ order plays the role of the reference field. The two beams propagate along a common optical path, thus significantly reducing the longitudinal phase noise.

It is to be understood that other interferometric configurations, whether common-path or otherwise, are within the scope of the present invention. A reference beam may be split off illuminating beam 13 before traversing sample S, for example, and combined with the scatter signal so as to fall jointly at CCD plane 20. A common-path configuration, however, may provide the foregoing advantage of stability.

Defining the direction of spatial modulation by the grating as along the x-axis, the total field at the CCD plane 20 has the form $$U_{CCD}(x, y) = |U_0|e^{i(\phi_0+\beta x)} + |U_1(x, y)|e^{i\phi_1(x, y)}. \quad (1)$$

In Eq. 1, $|U_{0,1}|$ and $\phi_{0,1}$ are the amplitudes and the phase of the orders of diffraction 0, 1, while $\beta$ represents the spatial frequency shift induced by the grating to the $0^{th}$ order. To preserve the transverse resolution of the microscope 16, the spatial frequency $\beta$ exceeds the maximum frequency allowed by the numerical aperture of the instrument. The $L_1$-$L_2$ lens system has an additional magnification, such as a magnification of $f_2/f_1=5$, so that the sinusoidal modulation of the image is sampled by a plurality of CCD pixels per period, preferably on the order of 6.

The signal derived from the interferogram at the CCD array is spatially high-pass filtered to isolate the cross term, $|U_0||U_1(x, y)|\cos[\phi_1(x, y)-\phi_0-\beta x]$, which can be regarded as the real part of a complex analytic signal. The imaginary component, $\sin[\phi(x,y)-\phi_0-\beta x]$, is obtained via a spatial Hilbert transform, as described by Ikeda et al., *Hilbert phase microscopy for investigating fast dynamics in transparent systems, Opt. Letters*, vol. 30, pp. 1165-67 (2005), which is incorporated herein by reference. Thus, from a single CCD exposure, the spatially-resolved phase and amplitude associated with the image field may be obtained, and a tangible image of either the amplitude or the phase, or both, may be displayed, as illustrated in multiple examples discussed below.

This measurement, in that it is performed in the image plane of a microscope rather than the Fourier plane, offers important advantages in the case of the thin samples of interest here. The signal sampling, phase reconstruction and unwrapping are more robustly performed in the image plane than in the Fourier or Fresnel zone, where high-frequency interference patterns and phase discontinuities may occur. Further, in the image plane of a thin and transparent sample, such as live cells, the intensity is evenly distributed, which utilizes efficiently the limited dynamic range of the CCD.

FTLS may be applied across a broad range of spatial scales, ranging from microscopic (organelles and cells) to macroscopic (organ) scales. As an example, the application of FTLS to dilute microsphere water suspensions, sandwiched between two cover slips is now described. The measured complex field associated with such samples can be expressed as $$U(r;t) = \int\int_A U_F(r')\sum_{i=1}^{N}\delta\{[r-r_i(t)]-r'\}d^2r' \quad (2)$$

In Eq. 2, $U_F$ is the (time-invariant) complex field associated with each particle, $\delta$ is the 2D Dirac function describing the position $(x_i, y_i)$ of each of the N moving particles, and the integral is performed over the microscope field of view A.

Figures 2A, 2B:
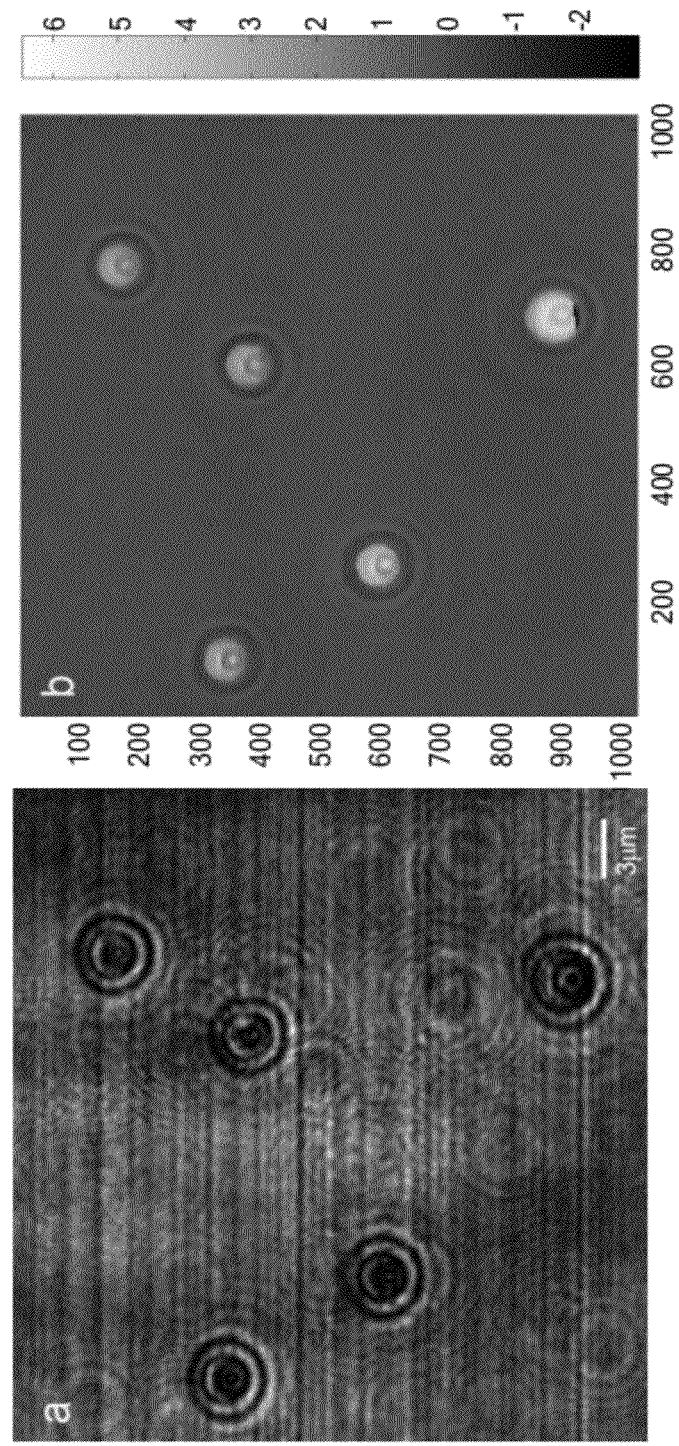
FIGS. 2a-2b show amplitude and phase distributions, respectively, obtained by imaging five 3-micron polystyrene beads in accordance with an embodiment of the invention.
Figure 2C:
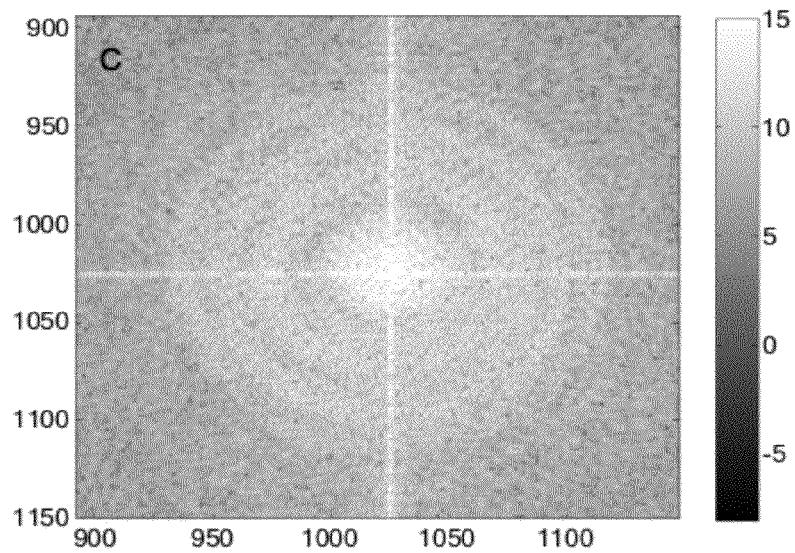
FIG. 2c shows the intensity distribution $|\tilde{U}(q)|^2$ corresponding to the amplitude and phase distributions of FIGS. 2a-2b.

FIG. 2a-b shows tangible images of the amplitude and phase distributions obtained by imaging 3-micron polystyrene beads at a particular point in time. The scattered far-field is obtained by Fourier transforming Eq. 2 in space. This angular field distribution factorizes into a form field $\tilde{U}_F$, which is determined by the angular scattering of a single particle, and a structure field $\tilde{U}_S$, describing the spatial correlations in particle positions, $$\tilde{U}(q;t)=\tilde{U}_F(q)\tilde{U}_S(q), \quad (3)$$

where q is the spatial wave vector. FIG. 2c shows the resulting intensity distribution $|\tilde{U}(q)|^2$ for the beads in FIGS. 2a-2b. As expected for such a sparse distributions of particles, the form function is dominant over the entire angular range. However, by finding the phase-weighted centroid of each particle, FTLS can retrieve the structure function whenever it has a significant contribution to the far-field scattering, e.g. in colloidal crystals.

Figure 2D:
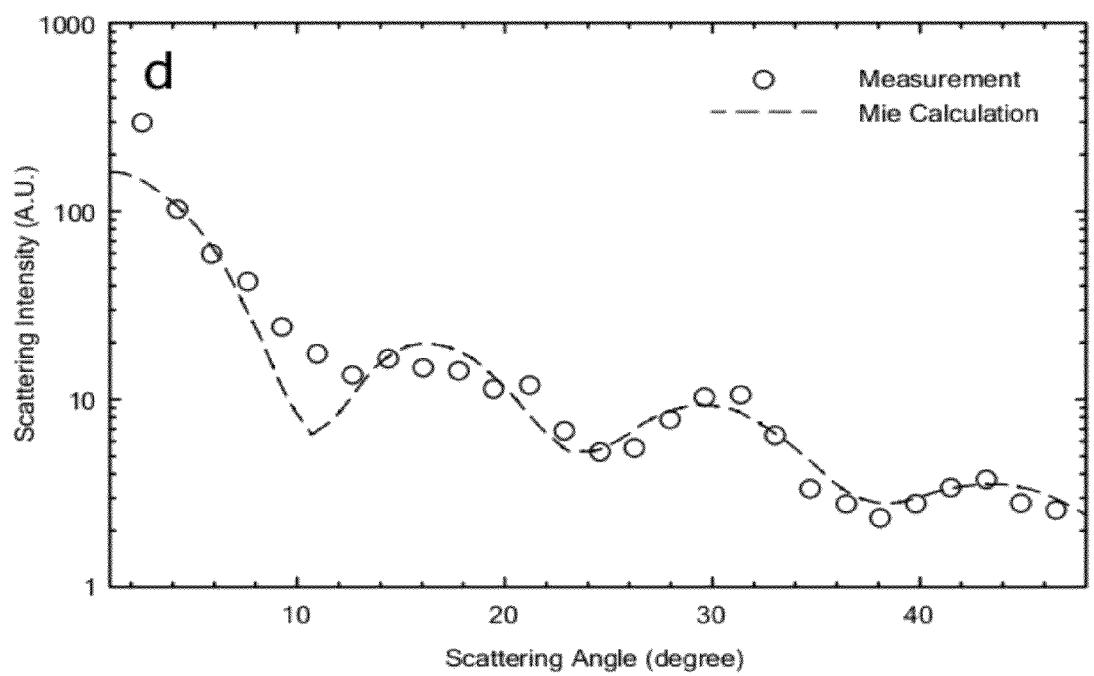
FIG. 2d and FIG. 3 compare experimental results of scattering intensity vs. angle with Mie theory for 5 beads, in FIG. 2d, and for 1, 3, 6, and 11 beads, in FIG. 3.
Figure 3:
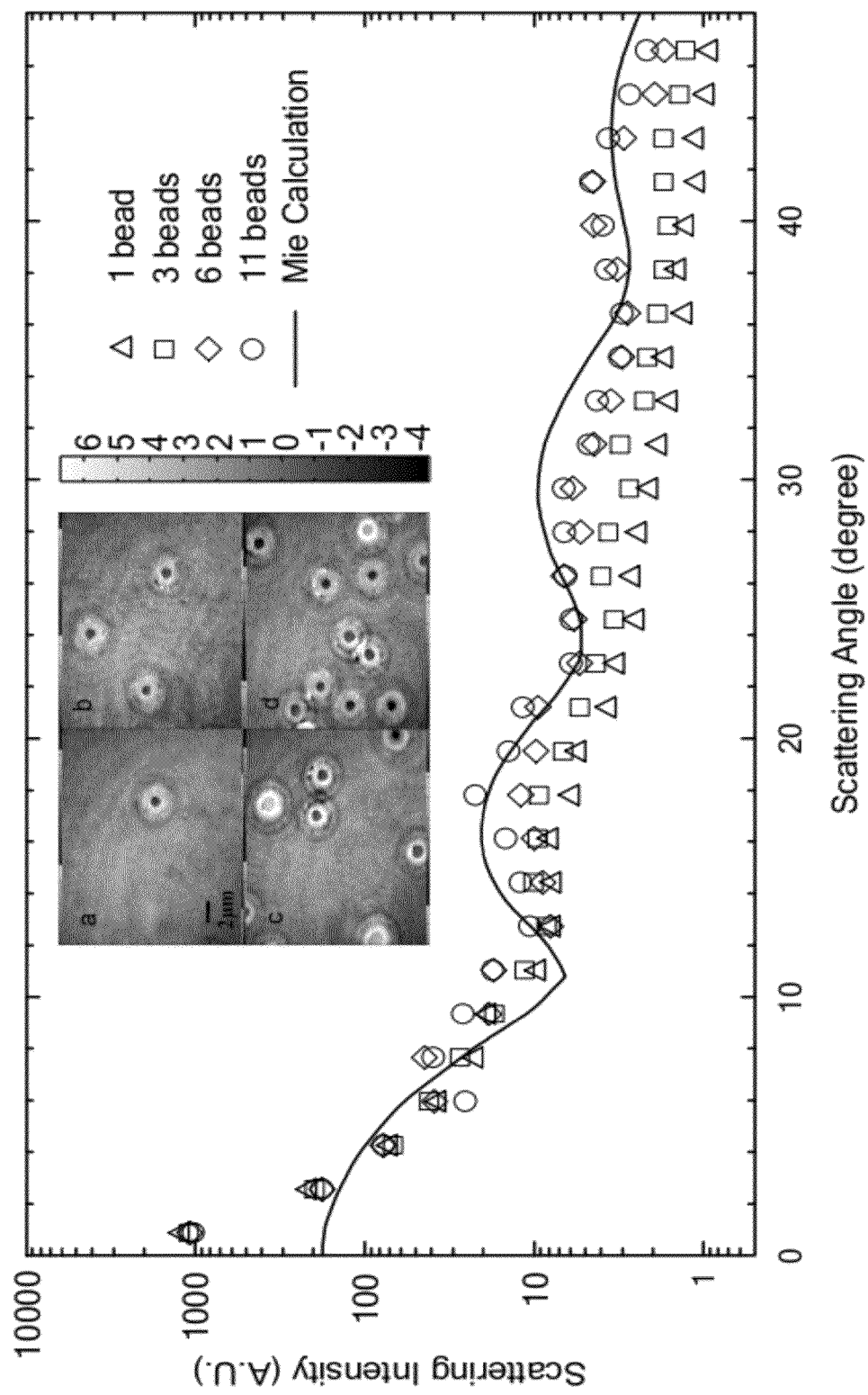

In order to demonstrate the ability of FTLS to retrieve quantitatively the form function of the spherical dielectric particles, Mie theory (as described in van de Hulst, *Light Scattering by Small Particles*, (Dover, 1981), incorporated herein by reference) may be used for comparison. The scattered intensity (as shown, for example, in FIG. 2c) is averaged over rings of constant wave vectors, $q=(4\pi/\lambda)\sin(\theta/2)$, with $\theta$ the scattering angle. To demonstrate the sensitivity of FTLS to weakly scattering objects, a systematic comparison between the measured angular scattering and Mie theory was performed for various numbers of beads within the field of view. These results are summarized in FIG. 2d and in FIG. 3. These data show that FTLS background noise is significantly below the scattering signal from a single particle. The expected oscillations in the angular scattering become significant as the number of beads increases, establishing the quantitative FTLS measurement.

Since angular measurements are obtained from one single CCD exposure (typically requiring no more than several milliseconds for readout), the technique of the present invention may advantageously provide high-throughput, thereby allowing dynamic studies to be performed as well. In particular, acquisition of sets of time-lapse phase and amplitude images provides for studies of dynamic light scattering signals from micron-sized particles undergoing Brownian motion.

Thus, the power spectrum of the scattered intensity can be expressed for each wave vector as $$P(q, \omega)=|\int\tilde{U}(q, t)e^{-i\omega t}dt|^2. \quad (4)$$

Figure 4A:
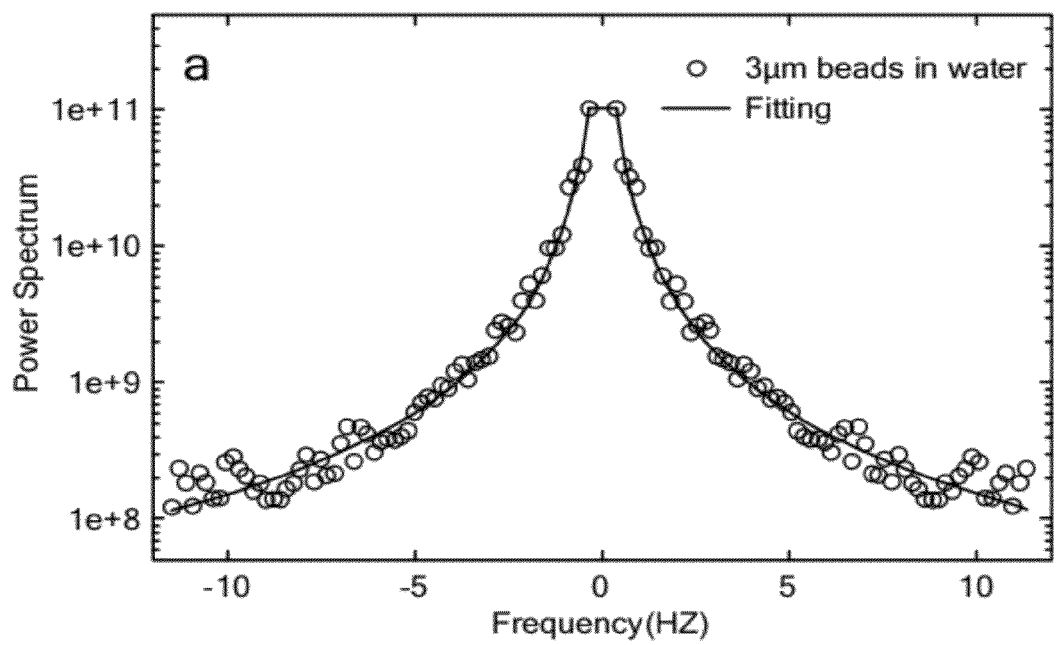
FIGS. 4a-4c show the power spectra associated with 1 μm and 3 μm beads in water and 25% by weight glycerol solution.
Figure 4B:
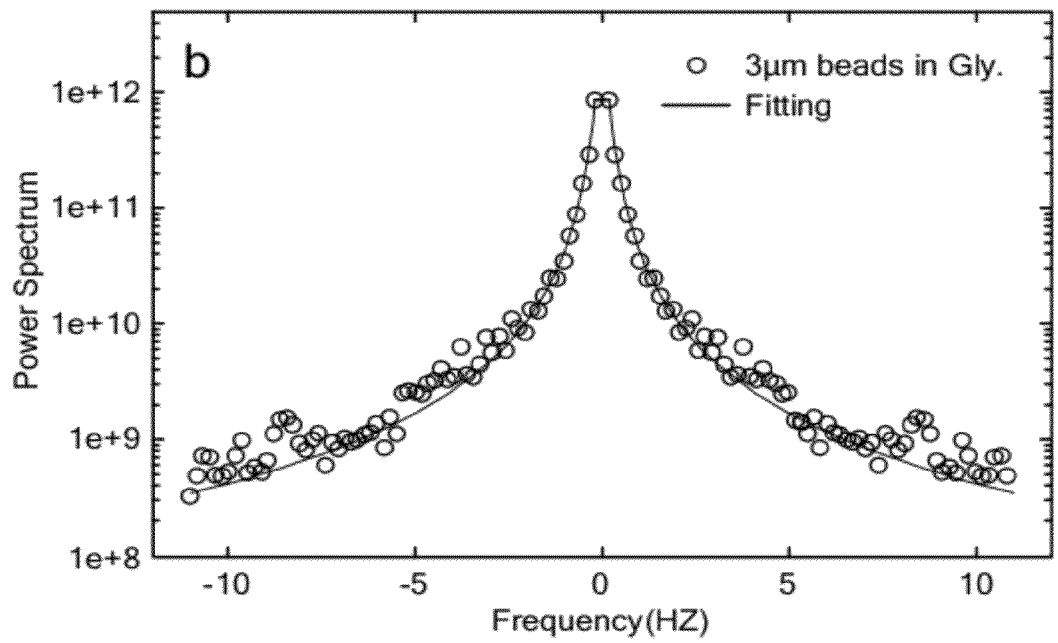
Figure 4C:
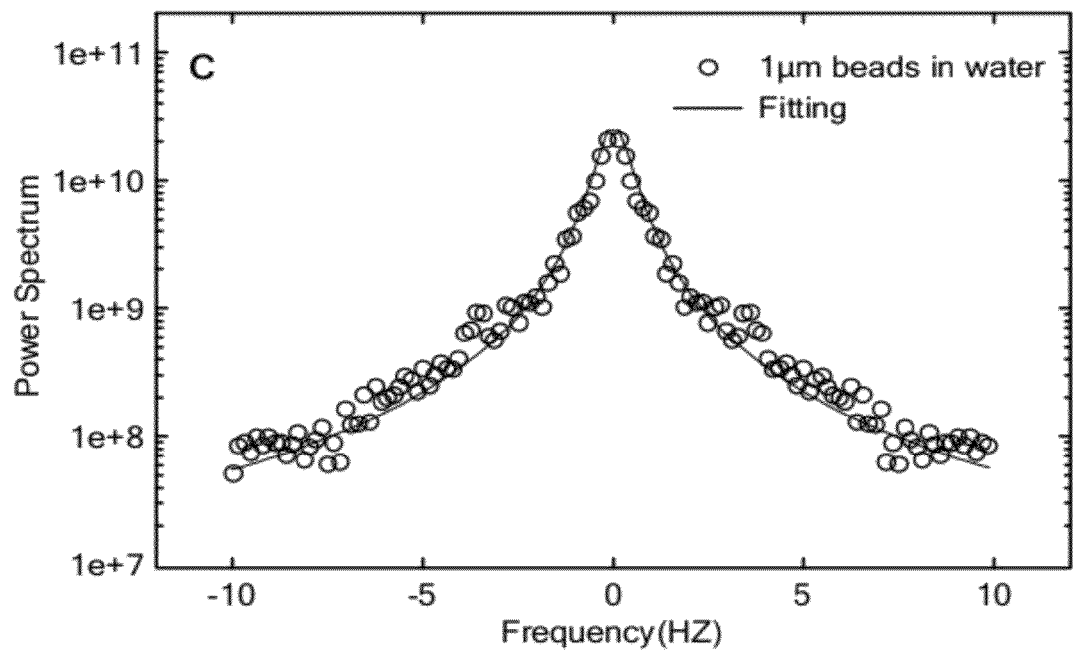

FIGS. 4a-c show the power spectra associated with 1-$\mu$m and 3-$\mu$m beads in water and 25%-by-weight glycerol solution. The experimental data are fitted with a Lorentzian function, which describes the dynamics of purely viscous fluids, $$P(q, \omega) \propto \frac{1}{1+(\omega/Dq^2)^2}. \quad (5)$$

Figure 4D:
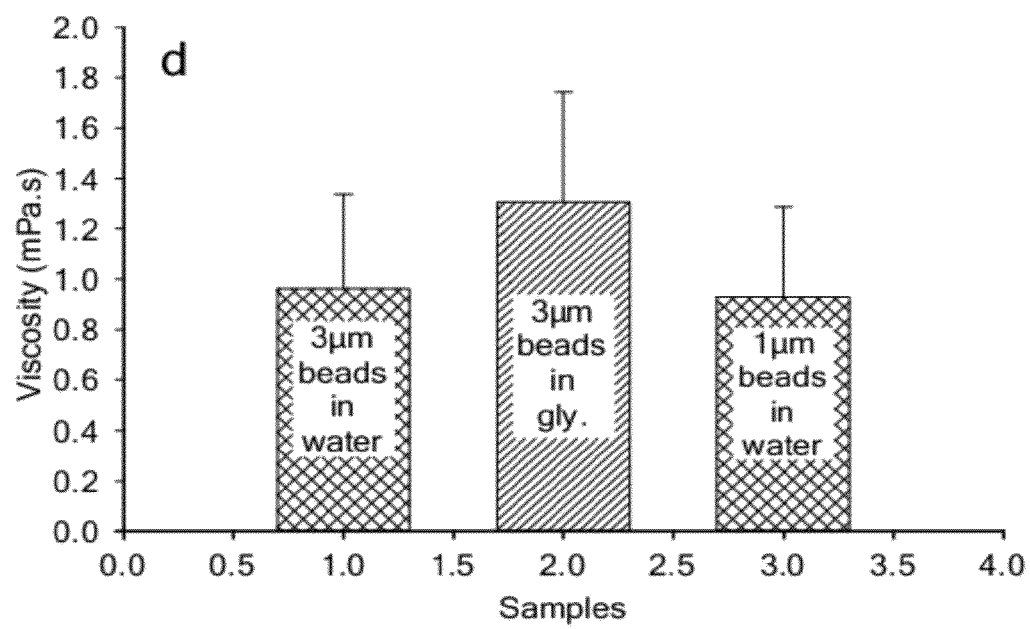
FIG. 4d summarizes the viscosity values measured in accordance with an embodiment of the present invention.

In Eq. 5, D is the diffusion coefficient, defined by $D=k_BT/4\pi\eta a$, with $k_B$ the Boltzmann constant, T the absolute temperature, $\eta$ the viscosity and a the radius of the bead. Note the factor of 4 (instead of the typical 6) in the expression for D, which reflects that primary contributions to the dynamic signal in the present case come from the 2D motion of beads, as discussed by Amin et al., *Microrheology of red blood cell membranes using dynamic scattering microscopy, Opt. Express*, vol. 15, pp. 17001-09 (2007), which is incorporated herein by reference. During measurements, the number of beads was constant, such that this possible source of intensity fluctuations was suppressed. The fits with Eq. 5 describe the data very well and allow for extracting the viscosity of the surrounding liquids as the only fitting parameter. The measured viscosity values are summarized in FIG. 4d. These values are the result of averaging the output of the fit over the entire angular range measured. The good agreement demonstrates that FTLS may advantageously quantify the dynamics of particles in thermal motion.

From the spatio-temporal FTLS data, the imaginary part of the complex shear moduli associated with water and glycerol, was inferred as follows. The normalized second order correlation function is calculated as:

$$g^{(2)}(q, \tau) = \frac{\langle|\tilde{U}(q, t)|^2 \tilde{U}(q, t+\tau)|^2\rangle}{\langle|\tilde{U}(q, t)|^4\rangle}. \quad (6)$$

The Siegert relationship connects the intensity autocorrelation function with the field autocorrelation function $g^{(1)}(\tau)$, $$g^{(2)}(\tau)=1+[g^{(1)}(\tau)]^2, \quad (7)$$

by virtue of the fact that the optical fields in the present case are fully coherent. Thus, $g^{(1)}$ can be obtained from Eq. 7 and further used to infer the particle mean-squared displacement $\langle \Delta r^2(\tau) \rangle$ as $$\langle \Delta r^2(\tau) \rangle = -\frac{6}{q^2} \ln[g^{(1)}(\tau)]. \tag{8}$$

The power spectrum of the mean-squared displacement, $\langle \Delta r^2(\omega) \rangle$, may then be obtained by taking the Fourier transform of $\langle \Delta r^2(\tau) \rangle$. The fluctuation-dissipation theorem (FDT) relates the $\langle \Delta r^2(\omega) \rangle$ to the loss response $\chi''(\omega)$, $$\chi''(\omega) = \frac{\omega}{2k_b T} \langle \Delta r^2(\omega) \rangle \tag{9}$$

The storage response function $\chi'(\omega)$ is related to $\chi''(\omega)$ by the Kramers-Kronig relation, which expresses the causality of the system $$\chi'(\omega) = \frac{2}{\pi} P \int_0^\infty \chi''(\xi) \frac{\xi}{\xi^2 - \omega^2} d\xi, \tag{10}$$

with P indicating a principal value integral. The shear modulus $G(\omega)$ is, thus, related to the response function $\chi(\omega)$ by the generalized Stokes-Einstein relationship, $$G(\omega) = \frac{1}{6\pi a} \frac{1}{\chi(\omega)}. \tag{11}$$

Figure 5A:
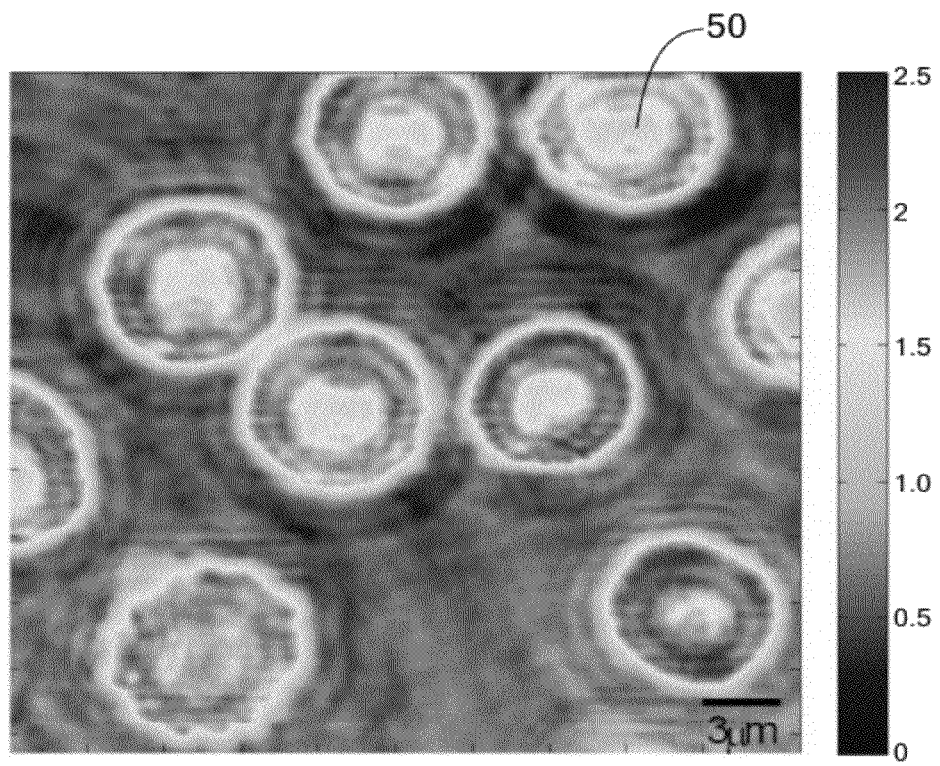
FIG. 5a shows a quantitative phase image of red blood cells between two cover slips, showing an identifiable "dimple" shape.
Figure 5B:
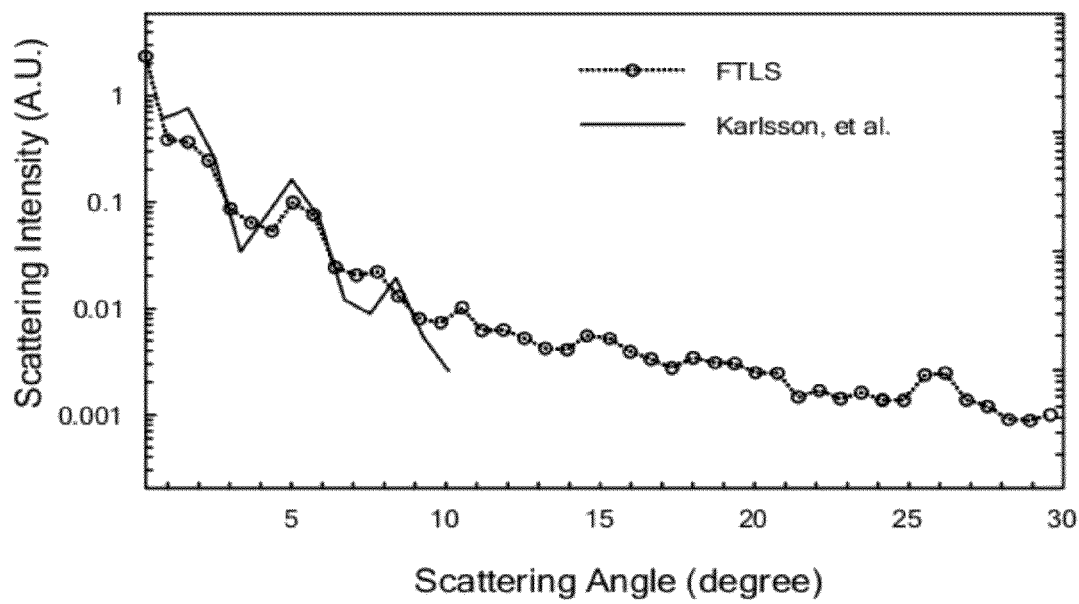
FIG. 5b depicts angular scattering corresponding to FIG. 5a, in comparison with a finite difference time domain simulation.

Referring, now, to FIGS. 5a and 5b, FTLS has been employed to determine experimentally the scattering properties of red blood cells (RBCs) 50, as may advantageously provide for optical testing of various blood constituents, as discussed by Faber et al., *Oxygen Saturation-Dependent Absorption and Scattering of Blood*, Phys. Rev. Lett., vol. 93, 028102 (2004), which is incorporated herein by reference. FIG. 5a shows a quantitative phase image of RBCs 50 prepared between two cover slips, with the identifiable "dimple" shape correctly recovered. The corresponding angular scattering is presented in FIG. 5b, comparing the measurements using the present invention with the results of a finite difference time domain (FDTD) simulation previously published by Karlsson, et al., *Numerical Simulations of.*, IEEE Transactions on Biomedical Engineering, vol. 52, pp. 13-18 (2005), which is incorporated herein by reference. Significantly, over the 10-degree range available from the simulation, the FTLS measurement and the simulation overlap very well.

FTLS may be used with various techniques that allow phase maps to be derived in the image plane of a microscope. In particular, techniques in accordance with embodiments of the present invention that preserve the spirit of phase contrast (PC) microscopy, yet, at the same time, render quantitative phase maps across and through transparent samples, are now described. Such quantified optical path-length shifts, in conjunction with nanometer-scale measurements, have broad application in the life sciences. Besides the $\pi/2$ shift introduced in typical PC microscopy, embodiments of the present invention may generate not only a phase shift of $\pi/2$ but additional spatial modulation, and may record additional images for each phase map.

Quantifying cell-induced optical path-length shifts allows for nanometer scale measurements of structures, including live cells and thin films, for example, and also of motions associated with such structures, in a non-contact, non-invasive manner. In accordance with the present invention, a highly sensitive imaging technique, which may also be referred to herein as "spatial light interference microscopy," or "SLIM," retrieves nanoscale information via interferometry. SLIM preserves the spirit of Zernike's PC method by using the same white light source and at the same time renders quantitative phase maps across transparent samples with sub-nanometer accuracy in both time and space. Because of the extremely short coherence length of this illumination light, which may be smaller than approximately 10 μm, but is preferably less than approximately 1.2 μm, SLIM allows for optical sectioning, which is to say that SLIM allows a three-dimensional view of live cells, without employing reconstruction numerical algorithms. Further, due to its intrinsic stability, SLIM quantifies nanometer motions in the cell over a broad time scale, from fractions of a second to days. In particular, SLIM measures quantitatively the spatially-resolved cell membrane fluctuations and, thus, retrieves the membrane tension in an adherent cell for the first time in a non-contact manner.

The present invention also teaches apparatus and methods for transforming a commercial PC microscope, such as a Zeiss Axio Observer Z1, for example, into a quantitative phase instrument. One unique feature of certain embodiments of the present invention is the use of a white light source 60 (shown in FIG. 6a) that originally equips conventional phase contrast microscopes. This brings along significant advantages. First, due to the absence of speckle, the background in the images is very flat, i.e. the spatial distribution of noise is very low, down to 0.3 nm path-length. Second, the small coherence length, which may be smaller than 10 microns, or, typically ~1 micron, for example, allows for optical sectioning through live cells, which is especially appealing in this "full-field" geometry. The enhanced phase contrast capabilities are demonstrated with imaging both nanostructures and live cells in both static and dynamic conditions.

Figure 6A:
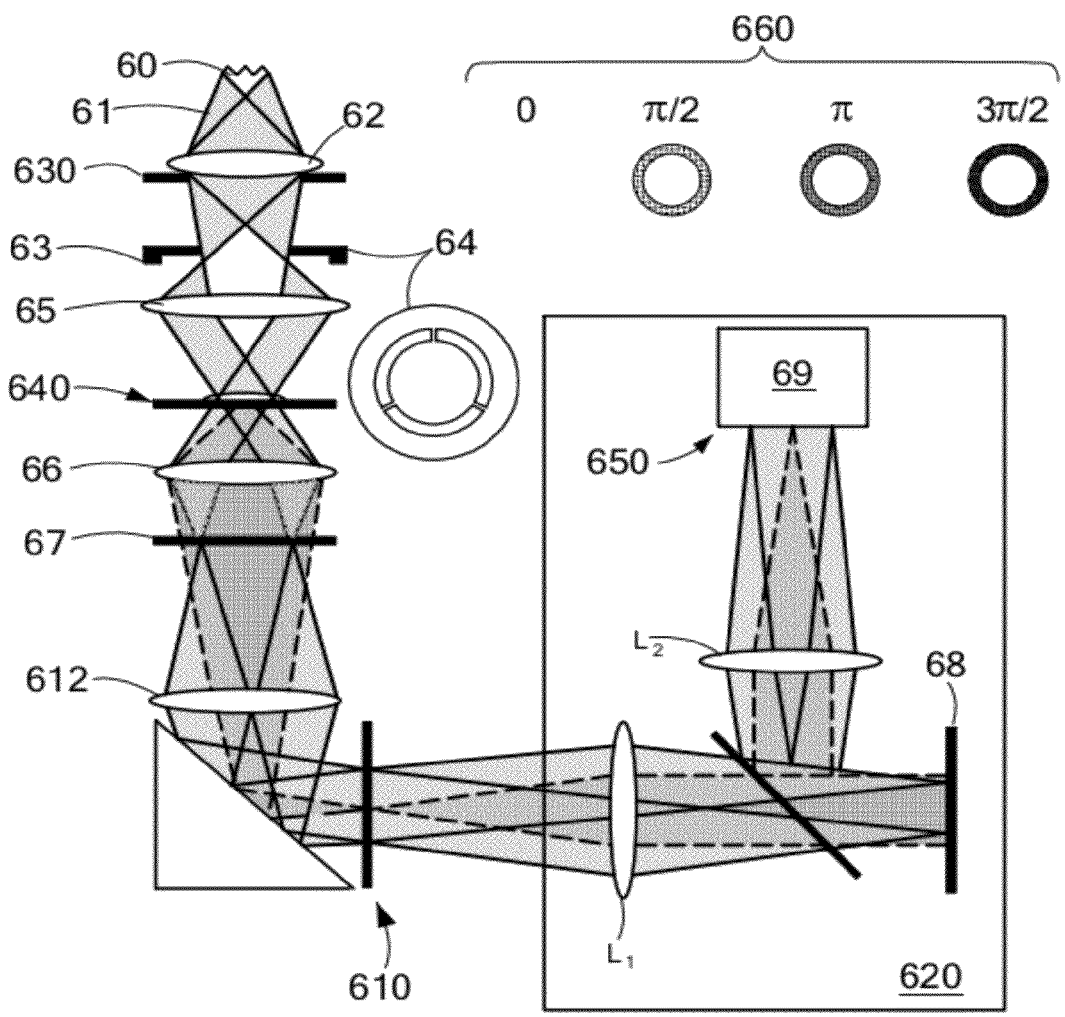
FIG. 6a is a schematic depiction of a quantitative phase contrast microscope in accordance with an embodiment of the present.

Embodiments of the present invention provide a generalization of PC microscopy in that the "phase plate" is not limited to a fixed phase shift of $\pi/2$, but is, in fact, a completely flexible and controllable phase mask provided by a 2D phase modulator 68 (shown in FIG. 6a). Phase modulator 68 may be comprised of a liquid crystal spatial light modulator (SLM), deformable mirror, micromirror array, etc.

One apparatus that may be used to practice the present invention is now described with reference to FIG. 6a. Filament 60 is exemplary of a broadband light source, which, indeed, may be chosen from among any sources such as LASERs, LEDs, or fiber-coupled output. Light 61 from filament 60 is collected by a collector lens 62 and sequentially the filament 60 itself is imaged onto a condenser annulus 64. Condenser annulus 64 is typically located at the focal plane of condenser 65, such that collimated light after the condenser will be focused by an objective 66 at its back focal plane 67. For a conventional phase contrast microscope, a phase objective with a built-in phase ring is used in order to introduce additional phase delay (typically $\pi/2$ for the center wavelength), and to introduce additional attenuation for undiffracted light (usually by a factor of 5). The phase image is then delivered at an interim image plane 610 and received by a charge-coupled device (CCD) or other focal plane imaging modality, or, alternatively, the interim image plane 610 may directly serve as the object of the eyepiece.

In accordance with the present invention, either a phase objective or common bright field objective can be used in the microscope, since the back focal plane 67 is sequentially imaged by the tube lens 612 and Fourier lens $L_1$, which is relayed onto the SLM 68. SLM 68 may be a reflective liquid crystal phase modulator (LCPM), for example, though any phase modulation modality is included within the scope of the present invention. In the present description, "LCPM" may be used, interchangeably with "SLM", and without limitation, to represent any form of phase modulation modality that is applied.

The active pattern on the LCPM is designed to precisely match the size and position of the phase ring image, such that additional phase delay can be applied controllably between the scattered and unscattered components of the image field. By displaying different masks on the SLM, one may directly modulate the phase or amplitude, or both, of frequency components of the image. The Fourier lenses $L_1$ and $L_2$, together with a SLM and focal plane array 69, comprise an optical module 620, referred to herein as a "SLIM module," which serves as a complementary component to a conventional microscope, for practice of the present invention.

On inspection of the light path, it should be apparent that there are two sets of conjugate planes: one set is formed by filament 60, aperture 63, back focal plane 67 of the objective 66 and the plane of SLM 68; the other set is formed by field diaphragm 630, specimen plane 640, interim image plane 610 and CCD plane 650.

For spatially coherent imaging systems, after passing the specimen (not shown, but disposed substantially in specimen plane 640), a portion of the light remains undiffracted and, in fact, forms a uniform background of the image; the other portion is scattered and contains the fine structure information of the specimen. The image is in fact an interferogram as seen in Eq. 12. Because, for transparent samples (e.g. most biologic samples), the phase difference $\Delta\phi(x, y)$ is small, a traditional phase contrast microscope introduces an additional phase shift $\phi=\pi/2$. Thus, the intensity distribution becomes:

$$I(x, y; \phi) = |E_0|^2 + |E_1(x, y)|^2 + 2|E_0||E_1(x, y)|\cos[\Delta\phi(x, y) + \phi] \quad (12)$$

Figure 6B:
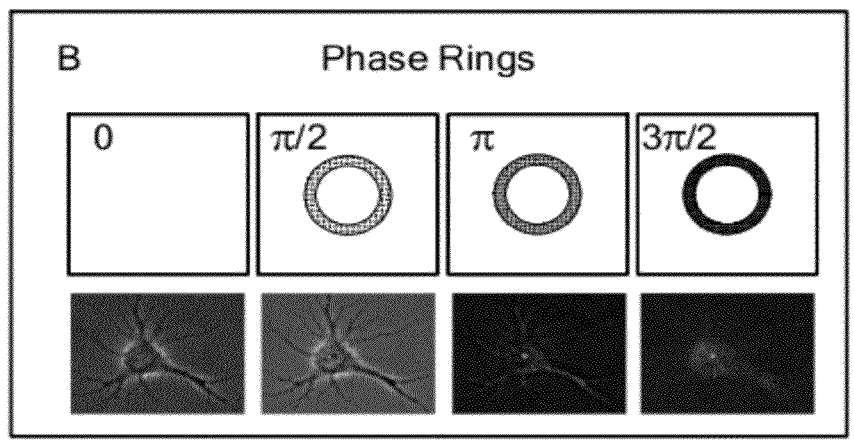
FIG. 6b shows images obtained at each of four phase ring settings, in accordance with an embodiment of the present.
Figure 6C:
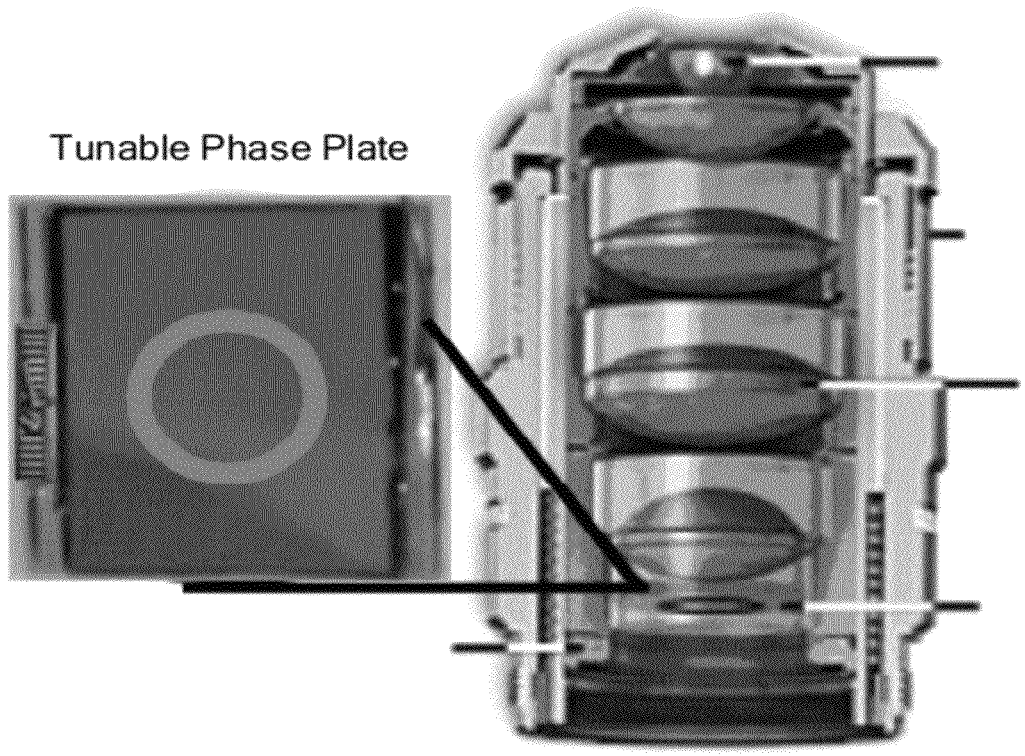
FIG. 6c is a cross-sectional view of a phase contrast microscope objective module containing a tunable phase plate in accordance with embodiments of the present invention.

However, for conventional phase contrast, no quantitative phase information can be obtained. By introducing the SLM into the optical path, spatial filtering may be performed with four different phase masks 660 as shown in FIGS. 6a and 6b. The effect of the SLM can be understood as a phase object with little amplitude modulation.

In some embodiments of the present invention, the tunable phase plate may be included within an objective module that couples directly to an existing phase contrast microscope. Such an objective is shown in cross section in FIG. 6c. The tunable phase plate modulates an optical depth traversed by light through each of a plurality of pixels.

In order to obtain quantitative phase information, the LCPM is calibrated to decide the relationship between pixel grey values and phase modulation. The LCPM may be placed between two polarizers and its intensity transmission recorded as follows. The relative orientation of polarizer and analyzer is first changed by 45° so that the SLM will work in "amplitude modulation" mode. Then, the grayscale value is scanned from 128 to 255 (i.e. 8 bits). The modulation from pixel value 0 to 127 and from 128 to 255 is symmetric. Thus, it is necessary only to scan half of the pixel values. There are many possible combinations that will give modulation from 0 to $3\pi/2$. Two of them are shown below.

Figure 7:
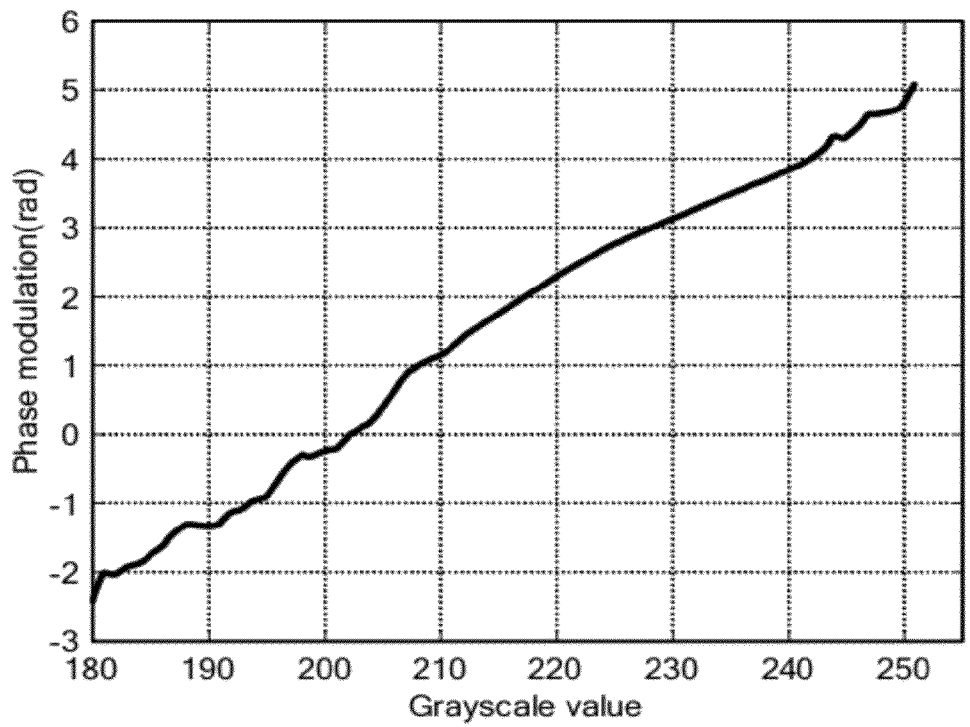
FIG. 7 shows a phase calibration of an SLM.

By scanning through the grayscale value from 0 to 255, we get the following amplitude modulation as follows (polarizer at 45 degrees, analyzer at 45 degrees):
The calibration plot is shown in FIG. 7.
Grayscale for phase modulation from 0, $\pi/2$, $\pi$, $3\pi/2$, to $2\pi$:

|  | Set 1 | | Set 2 | |
| --- | --- | --- | --- | --- |
| Relative Phase | Grayscale | Actual Phase | Grayscale | Actual Phase |
| 0 | 186 | −1.6735 | 210 | 1.1215 |
| $\pi/2$ | 202 | −0.0703 | 211 | 1.261 |
| $\pi$ | 213 | 1.4959 | 227 | 2.8897 |
| $3\pi/2$ | 229 | 3.0284 | 246 | 4.4559 |
| $2\pi$ | 247 | 4.6438 | | |

Figure 6D:
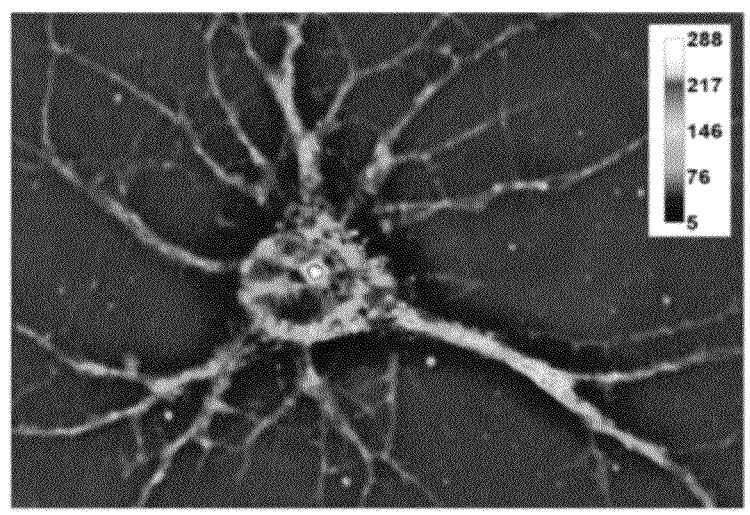
FIG. 6d is a quantitative phase image of a hippocampal neuron, obtained using methods of the present invention.

Once the respective phase-shifted interferograms are combined, in accordance with the description that follows, a quantitative phase image may be obtained, such as the quantitative phase image of a hippocampal neuron, shown in FIG. 6d. The phase mapped in FIG. 6d is proportional to $$\phi(x, y) = \frac{2\pi}{\lambda} \int_0^{h(x,y)} [n(x, y, z) - n_0]\, dz. \quad (13)$$

In Eq. 13, $n - n_0$ is the local refractive index contrast between the cell and the surrounding culture medium, h the local thickness of the cell, and $\lambda$ the central wavelength of the illumination light. SLIM provides the local phase shift $\phi$ with great accuracy, which in turn allows for detecting local changes in thickness h at a scale much smaller than the wavelength of light.

In order to understand the performance of the quantitative white light phase microscopy, one may first consider the following relations which obtain for a particular frequency $\omega$:

$$I(x, y, z; \omega) = |E^s(x, y, z; \omega) + E^i(x, y, z_i; \omega)|^2 = I^s(x, y, z; \omega) + I^i(x, y, z_i; \omega) + 2\operatorname{Re}[w(x, y, z; z_i; \omega)], \quad (14)$$

where the interference term $w(x, y, z; z_i, \omega) = E^s(x, y, z; \omega)E^{i*}(x, y, z_i; \omega)$. For spatially coherent light, according to Mandel and Wolf, *Optical Coherence and Quantum Optics* (1995) (incorporated herein by reference), one can always write down $w(k) = S(k)e^{j\Delta\phi}$, and thus $$w(x, y, z; z_i, k) = S(k)e^{j[k(z-z_i) + \Delta\phi(x, y, z)]} \quad (15)$$

Integrating Eq. 14 over k, we get $$\int w(x, y, z; z_i, k)\, dk = \int S(k)e^{j[k(z-z_i) + \Delta\phi(x, y, z)]}\, dk = e^{j\Delta\phi(x, y, z)}\Gamma(z-z_i) \quad (16)$$

where $\Gamma(z-z_i) = \int S(k)e^{jk(z-z_i)}\, dk$.

Now, it may be assumed that the central frequency of the power spectrum $S(k)$ may be referred to as $k_0$. For symmetric spectra, such $k_0$ is readily found, while for asymmetric spectra, the definition of $k_0$ requires further justification. In terms of $k_0$, $$\Gamma(z-z_i) = \int S(k-k_0)e^{j(k-k_0)(z-z_i)}\, dk = \hat{\Gamma}(z-z_i)e^{-jk_0(z-z_i)}, \quad (17)$$

where the envelope $\hat{\Gamma}(z-z_i) = \int S(k-k_0)e^{jk(z-z_i)}\, dk$ is a real function if we assume the spectra is symmetric. Thus, Eq. 13 may be integrated over all frequencies to obtain $$I(x, y, z_i) = I^s(x, y, z) + I^i(x, y, z_i) + 2\hat{\Gamma}(z-z_i)\cos[k_0(z-z_i) + \Delta\phi]. \quad (18)$$

By modifying the delay $z_i$, phase delays of $-\pi$, $-\pi/2$, 0 and $\pi/2$ may be obtained, indeed, many more combination exists, such as the above four frames plus $n\pi/2$ where n is an integer.

$$I(x, y; 0) - I(x, y; -\pi) = 2\left[\hat{\Gamma}(0) + \hat{\Gamma}(-\pi)\right]\cos(\Delta\phi); \text{ and} \quad (19)$$

$$I\left(x, y; -\frac{\pi}{2}\right) - I\left(x, y; \frac{\pi}{2}\right) = 2\left[\hat{\Gamma}\left(-\frac{\pi}{2}\right) + \hat{\Gamma}\left(\frac{\pi}{2}\right)\right]\sin(\Delta\phi). \quad (20)$$

Thus, as long as the following relationship obtains, $$\hat{\Gamma}(0) + \hat{\Gamma}(-\pi) = \hat{\Gamma}\left(-\frac{\pi}{2}\right) + \hat{\Gamma}\left(\frac{\pi}{2}\right), \quad (21)$$

e the relative phase may be derived as $$\Delta\phi(x, y) = \tan^{-1}\left[\frac{I(x, y, ; -\pi/2) - I(x, y; \pi/2)}{I(x, y; 0) - I(x, y; -\pi)}\right]. \quad (22)$$

Defining $\beta(x, y) = |E^s(x, y)|/|E^i|$, the phase associated with the image field $E(x, y)$ can be determined as $$\phi(x, y) = \tan^{-1}\left[\frac{\beta(x, y)\sin(\Delta\phi(x, y))}{1 + \beta(x, y)\cos(\Delta\phi(x, y))}\right]. \quad (23)$$

Figure 8:
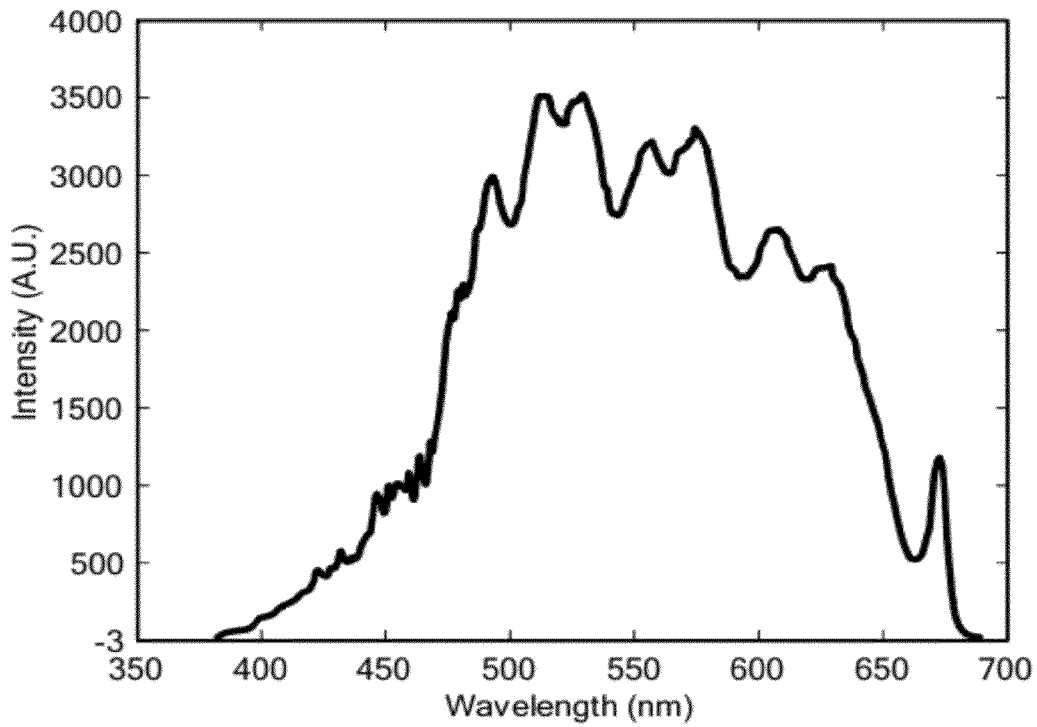
FIG. 8 is a measured power spectrum of a white source employed in accordance with an embodiment of the invention.

For a typical system employed in accordance with an embodiment of the present invention, the power spectrum $A^2(\omega)$ of the illumination source is shown in FIG. 8.

Based upon measurement, information with respect to the complex field at center frequency $\omega_0$, i.e., $E^s_f(x, y, z_0; \omega_0)$ may be determined, as now further discussed.

The incident field is a plane wave propagating along the $\vec{k}_0$ direction:

$$E^i(\vec{r}; \vec{k}_0) = A(\omega)e^{j\vec{k}_0 \cdot \vec{r}}. \quad (24)$$

The scattered field, in turn, under a first-order Born approximation, may be represented as:

$$E^s(\vec{r}; k) = \int_V E^i(\vec{r}'; k) F(\vec{r}'; k) \frac{e^{jk|\vec{r}-\vec{r}'|}}{|\vec{r}-\vec{r}'|} d^3r', \quad (25)$$

where the scattering potential of the medium $$F(\vec{r}; k) = \frac{1}{4\pi}k^2\left[n^2(\vec{r}; k) - 1\right] = \frac{1}{4\pi}k^2\chi(\vec{r}, k).$$

Following the discussion of Born and Wolf, the scattered field may be expressed using an angular spectrum representation at plane $z_0$ according to $$E^s(x, y, z_0, \vec{k}_0; k) = \quad (26)$$

$$\int\int_{-\infty}^{\infty} \frac{jA(k)}{2\pi k_z} \tilde{F}(\vec{k}-\vec{k}_0; k) e^{j(k_x x + k_y y + k_z(k)z_0)} dk_x dk_y$$

Where the 3D Fourier transform of the scattering potential is $\tilde{F}(\vec{k}-\vec{k}_0; k) = \int_V F(\vec{r}'; k)e^{j(\vec{k}-\vec{k}_0)\cdot\vec{r}'}d^3r'$, i.e., and $k_z(k) = \sqrt{k^2 - k_x^2 - k_y^2}$. From Eq. 24, with the 2D Fourier transform of $E^s(\vec{r}; k)$ defined as $\tilde{E}^s(k_x, k_y; z, k)$, we have $$\tilde{E}^s(k_x - k_{0x}, k_y - k_{0y}; z_0, k) = j2\pi A(k)k_z^{-1}e^{jk_z z_0}\tilde{F}(\vec{k}-\vec{k}_0, k). \quad (27)$$

Now, if $P(x, y; k)$ represents the spatial coherent point spread function of a 4f imaging system (described, for example, in Goodman, *Introduction to Fourier Optics* (1996), herein incorporated by reference), the scattered field at the image plane will be the convolution of the field $E^s(x, y, z_0; k)$ and $P(x, y; k)$, namely:

$$E^s_f(x, y, z_0; k) = E^s(x, y, z_0; k) * P(x, y; k) = \iint_{-\infty}^{\infty} E^s(x', y', z_0; k)P(x-x', y-y'; k)dx'dy'. \quad (28)$$

Applying a 2D Fourier transform to both sides of Eq. 27 yields:

$$\tilde{E}^s_f(k_x, k_y; k_{0x}, k_{0y}; z_0, k) = \quad (29)$$

$$\frac{j2\pi A(k)e^{jk_z(k)z_0}}{k_z(k)}\tilde{F}(\vec{k}-\vec{k}_0, k)\tilde{P}_u(-k_x, -k_y; k).$$

where $\tilde{P}_u(-k_x, -k_y; k)$ is the pupil function of the system, which is not related to frequency as long as the system is achromatic. Explicitly, for such an achromatic system, the pupil function can be written as $\tilde{P}_u(-s_x, -s_y)$. New space variables may be introduced for the image space, since we are only considering the field at the front focal plane of the objective, which will be relayed with fidelity to the back focal plane of the tube lens. Thus, the same notations may be used for image space and object space. The incident field will remain as a plane wave, namely:

$$E^i_f(x, y, z_0; k) = A(k)e^{j(-k_{0x}x - k_{0y}y + k_{0z}z_0)}. \quad (30)$$

In the phase shifting interferometry described in accordance with certain embodiments of the present invention, a phase modulation SLM is used to introduce additional phase delays, and the corresponding field can be written as $$E^i_f(x, y, z_0; k) = A(k)e^{j(-k_{0x}x - k_{0y}y + k_{0z}z_0) - jkd}. \quad (31)$$

The final intensity is thus expressed as the sum of the interference patterns over all emitted frequencies:

$$I_f(x, y, z_0) = \int |E^s_f(x, y, z_0; k) + E^i_f(x, y, z_0; k)|^2 d\omega = \quad (32)$$

$$\int \{A^2(k) + [E^s_f(x, y, z_0; k)]^2 +$$

$$2A(k)\text{Re}\left[E^s_f(x, y, z_0; k)e^{-j[k_{0x}x + k_{0y}y + k_{0z}z_0] + jkd}\right]\}\left(\frac{d\omega}{dk}\right)dk.$$

Applying a 2D Fourier transform to both sides of Eq. 32 yields:

$$\tilde{I}_f(k_x, k_y, z_0) = (\int A^2(k)d\omega)\delta(k_x, k_y) + \tilde{B}(k_x, k_y, z_0) + \tilde{C}(k_x, k_y, z_0), \quad (33)$$

where $$\tilde{B}(k_x, k_y, z_0) = \iint\left[\int |E^s_f(x, y, z_0; k)|^2 d\omega\right]e^{-j(k_x x + k_y y)}dxdy, \text{ and} \quad (34)$$

$$\tilde{C}(k_x, k_y, z_0) = j2\pi\text{Re}\left[\tilde{P}_u(-s_x + s_{0x}, -s_y + s_{0y}) \quad (35)\right.$$

$$\left.\int \frac{A^2(k)e^{jkd}\tilde{F}(\vec{k}-k_{0z}\hat{z}; k)}{k_z(k)}e^{j[k_z(k)-k_{0z}]z_0}d\omega\right].$$

Taking the 1D Fourier transform of both sides of Eq. 35 with respect to $z_0$ yields:

$$\tilde{C}_\beta(k_x, k_y, \beta) = j2\pi \text{Re} \left[ \tilde{P}_u(-s_x + s_{0x}, -s_y + s_{0y}) \right. \quad (36)$$

$$\left. \int \frac{A^2(k)e^{jk\tau} \tilde{F}(\vec{k} - k_{0z}\hat{z}; k)}{k_z(k)} \delta\{\beta - [k_z(k) - k_{0z}]\} d\omega \right].$$

The delta function selects out $$k = \frac{-\beta^2 - k_x^2 - k_y^2}{2\beta}.$$

From the property of the delta function $$\delta[f(t)] = \sum_{i=1}^{n} \frac{1}{|f'(t_i)|} \delta(t - t_i)$$

one obtains:

$$\tilde{C}_\beta(k_x, k_y, \beta) = j2\pi \text{Re} \left[ \frac{\tilde{P}_u(-s_x + s_{0x}, -s_y + s_{0y})[A^2(k)e^{jk\tau}]\frac{d\omega}{dk}}{k_z(k) - k} \right. \quad (37)$$

$$\left. \left[ \tilde{F}(\vec{k} - k_{0z}\hat{z}; k) \right] \right]_{k=\frac{-\beta^2-k_x^2-k_y^2}{2\beta}}$$

The foregoing provides a recipe to obtain the function $\tilde{F}$:
1. Apply a 3D Fourier transform to obtain the function $\tilde{C}_\beta(k_x, k_y, \beta)$;
2. Divide $\tilde{C}_\beta(k_x, k_y, \beta)$ by the leading factors—based on the known point-spread function and illuminating spectrum—so as to obtain $\tilde{F}(k_x, k_y, \beta)$;
3. Apply an inverse 3D Fourier transform to get the 3D susceptibility distribution of the sample under study.

Illustrative Measurements

Figure 9A:
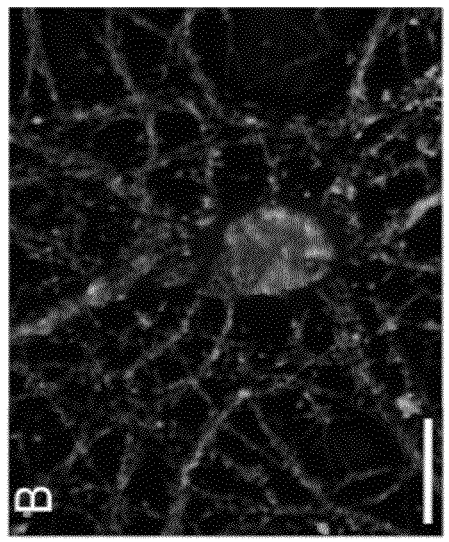
FIGS. 9A-9B are combined multimodal images of cultured neurons acquired through spatial light interference microscopy ("SLIM", shown in green) and fluorescence microscopy. Neurons were labeled for somatodendritic MAP2 (blue), and nuclei (red).
Figure 9B:
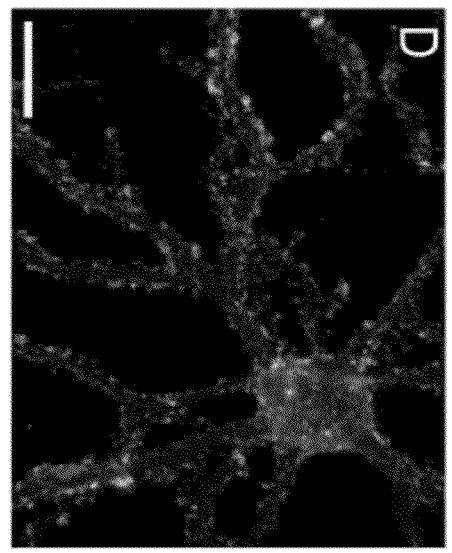
Figure 9C:
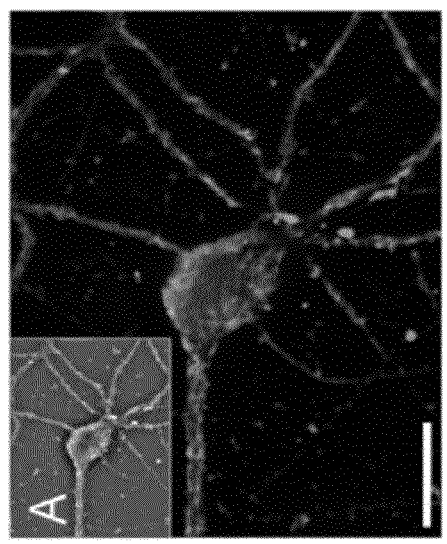
FIG. 9C plots optical path-length fluctuations along the dendrites (green) and axon (red) retrieved from the inset of FIG. 9A.
Figure 9D:
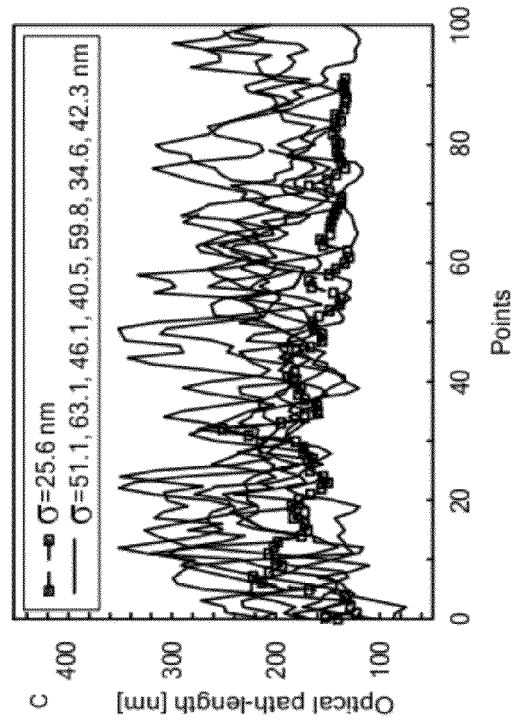
FIG. 9D shows synaptic connections of a mature hippocampal neuron (33 DIV) immunochemically labeled for synapsin (green), MAP2 (blue), and f-actin using rhodamine phalloidin (red). All scale bars are 20 μm.

A distinct feature of SLIM is that the quantitative phase image is intrinsically overlaid with all the other imaging channels of the microscope, such as epi-fluorescence, differential interference contrast, and, obviously, phase contrast, all provided as examples of complementary imaging channels Simultaneous fluorescence imaging complements SLIM's unique structural information with the ability to determine molecular specificity. In FIGS. 9A and 9B, SLIM images of axons and dendrites are shown, where fluorescent staining has been performed for somato-dendritic microtubule associated protein 2 (MAP2) of primary hippocampal neurons cultured for 19 days in vitro (DIV). Fine axonal processes are distinguished from dendrites, not only by the MAP2 label, but by SLIM where the quantitative phase imaging channel reveals changes in the local refractive index of structures reminiscent of actin-rich synaptic connections (FIG. 9B. As shown in FIG. 9C, these inhomogeneities are observed particularly along dendrites where the spines develop. In order to quantify these structural differences achieved by SLIM, we traced individual neurites using NeuronJ, a semi-automatic algorithm implemented in Java platform, and described by Meijering et al. in *Cytometry*, vol. 58A, p. 167 (2004), which is incorporated herein by reference. By quantifying the optical path-length fluctuations for each trace, the standard deviation of the path-length fluctuations along the axons, σ=25.6 nm, is found to be the lowest among all neurites. This result indicates that there are subtle inhomogeneities associated with the connecting synaptic structures, which can be revealed by SLIM as path-length changes. By 3 weeks in dispersed culture, the majority of dendritic spines mature to form presynaptic buttons on the dendritic shafts of hippocampal neurons. These are comparable to synaptic elaborations on a mature hippocampal neuron (33 DIV) with labeled f-actin, synapsin, and MAP2 (FIG. 9(D)). SLIM may thus advantageously offer a window into studying the dynamic processes associated with the formation and transition of collateral filiopodia into spines, and the dynamics of plasticity-related changes in spine structure. SLIM also reports dynamic activity of transport phenomena within neuronal processes.

Embodiments of the present invention may provide the following additional advantage: While fluorescence microscopy is sensitive to photobleaching, SLIM can be used to image live cells dynamics over extended periods of time, and provide quantitative information. For example, we imaged live cells in culture over more than 24 hours, without loss in performance or sample degradation. Indeed, the present invention advantageously provides for optical sectioning through a live cell with micron-scale resolution, without exogenous contrast agents.

3-D Reconstruction

Using the very short coherent length of white light (coherence gating), and by virtue of a high numerical aperture objective (depth of focus gating), the present invention provides 3D sectioning information in live cells. The system can be understood from the following intuitive picture: plane wave incident into the scattering sample; light was scattered by the sample and the scattered field propagated as spherical wave; unscattered light remain plane wave within first order Born approximation and interfere with the scattered field. Theoretical analyses show the imaging system now behaves like a band pass filter in k space (Fourier transform of the space vector r). Three-dimensional information of the sample may be obtained by z-slice sectioning with white light, which means tomography reconstruction is possible.

Figure 10:
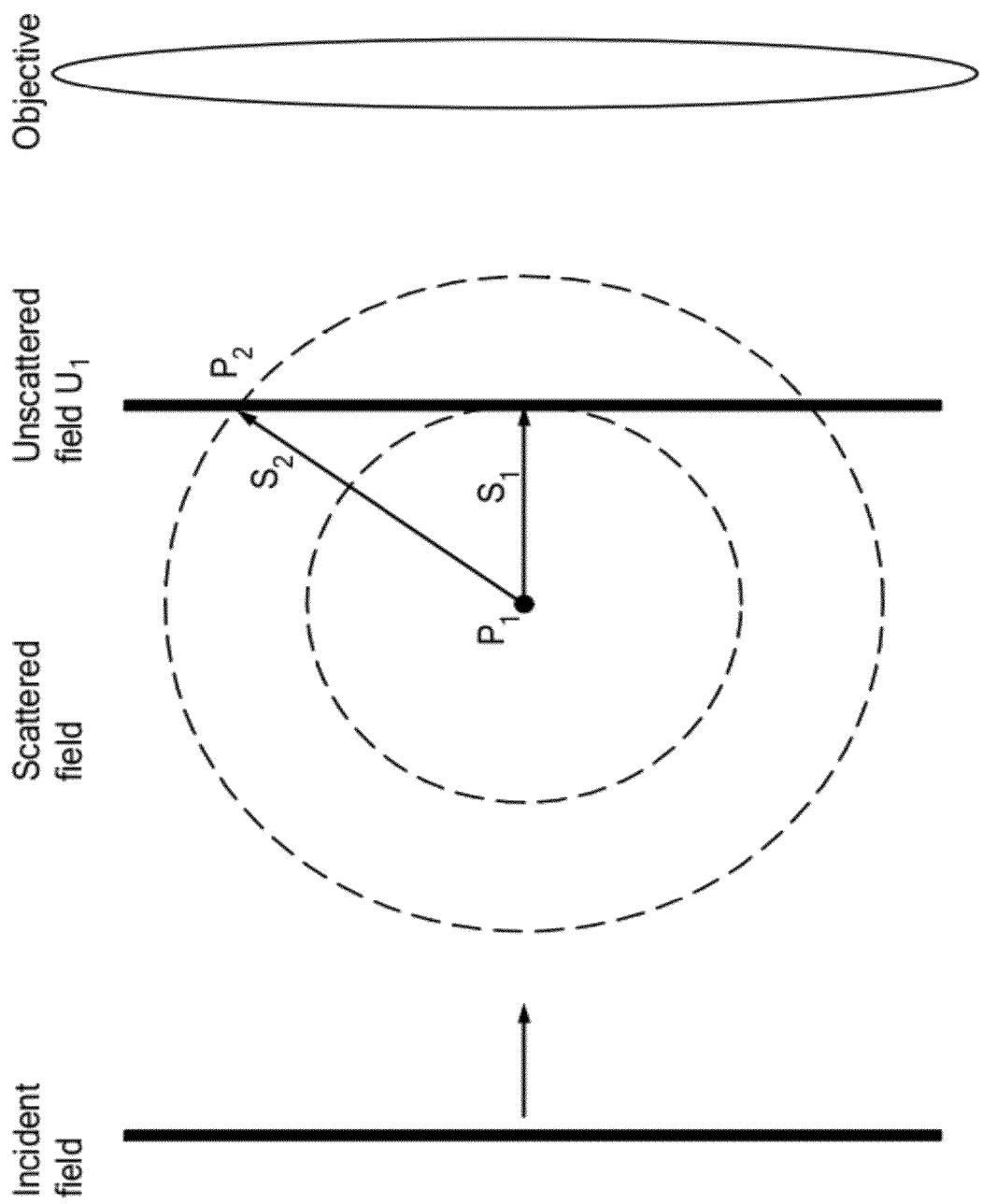
FIG. 10 is a schematic side view of the specimen as positioned within the illuminating field, for explication of 3D sectioning in accordance with embodiments of the present invention.

The combination of white light illumination, high numerical aperture (NA), and phase-resolved detection endow the invention with an ability to provide optical sectioning, as now described with reference to FIG. 10. The micron-range coherence length limits the extent to which scattering from various depths in the cell blurs the image. Light that is scattered from 2 points separated in depth by less than the coherence length will add at the image plane incoherently. Thus, upon phase shifting, this incoherent background remains constant and is therefore removed during the phase retrieval processing. Thus, in addition to suppressing the speckle effects that generally degrade laser light imaging, SLIM can provide depth-resolved imaging. SLIM's depth sectioning ability, discussed below and illustrated in FIG. 11, can be understood, with reference to FIG. 10, as follows: Consider two particles (scatterers) within the sample, at different z-positions: $P_1$ is out of focus and $P_2$ is in the plane of focus. Fields originating from $P_1$ contribute to $P_2$ in 2 different ways: first the field directly scattered from $P_1$ to $P_2$, of path-length $S_2$ and, second, the contribution from $P_1$ to the unscattered plane wave $U_1$, of path-length $S_1$. With laser illumination, these two field components interfere and generate a resulting field with a new phase, which averages the information from the two different points, i.e. there is no depth-resolving power. However, if the coherence length is shorter than the path-length difference $S_2-S_1$, the two fields add incoherently and, upon phase shifting, the out of focus contribution is removed. As can be seen in FIG. 10, the larger the angle of the $P_1-P_2$ path with respect to the optical axis, the larger the path-length difference $S_2-S_1$ and, thus, the stronger the sectioning. Therefore a high NA objective is preferred for better sectioning and 3D reconstruction.

Figure 11D:
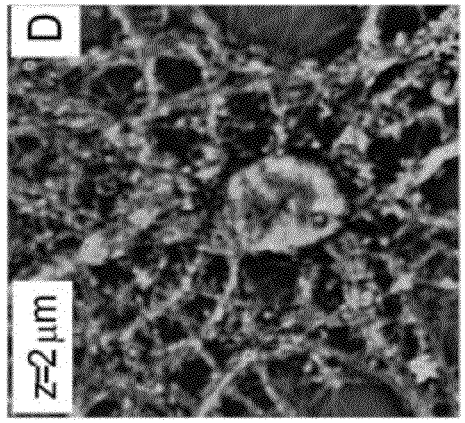
FIGS. 11D and 11E depict images of the same neuron at the depths indicated by the dash lines in FIG. 11C.
Figure 11E:
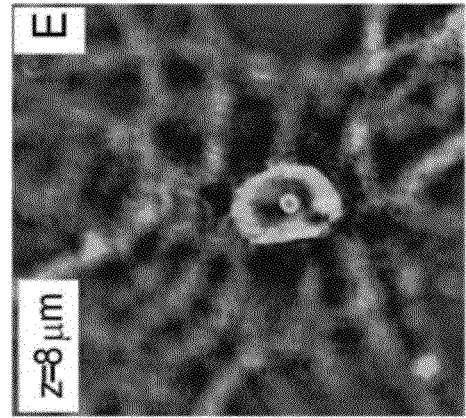
Figure 11B:
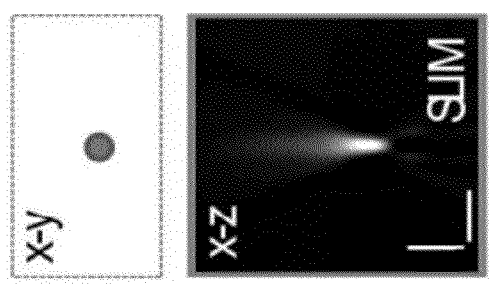
FIGS. 11A and 11B show depth-resolved quantitative phase imaging of 1 micron-diameter polystyrene particles using diffraction phase microscopy (DPM) (FIG. 11A) and SLIM (FIG. 11B). The scale bars indicate 2 microns in both directions.
Figure 11C:
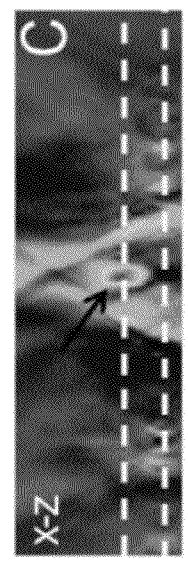
FIG. 11C is an x-z cut through a live neuron; the bottom of the image corresponds to the glass surface. The soma and nucleolus (arrow) are clearly visible.
Figure 11A:
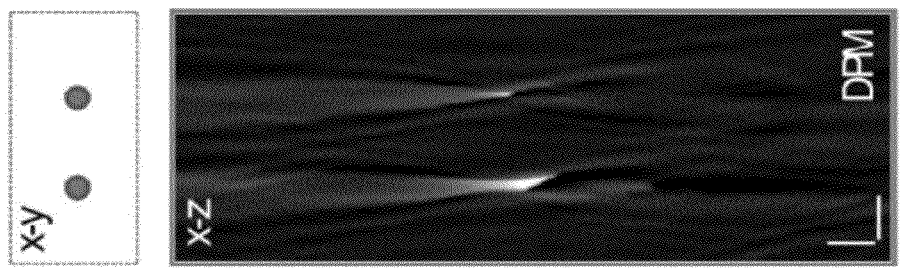

FIGS. 11A and 11B show a comparison between imaging in depth with the laser-based diffraction phase microscopy (DPM) quantitative phase technique and SLIM. Samples made of polystyrene beads of 1 μm diameter laying on a cover slip were scanned through the microscope focus in 0.2 μm steps. Due to the long coherence length of the laser illumination in DPM, the scattered and unscattered light interfere throughout the entire depth range. Thus, the result of this interference is a field with a broad phase distribution along the z axis, i.e. laser light offers no sectioning capability. By contrast, in SLIM the z-axis spread of the phase signal is tightly localized around the object, which is an indication of optical depth sectioning. This capability is illustrated by imaging live neurons in culture (FIGS. 11C-11E). While there is certain elongation along the z-axis, as indicated especially by the shape of the cell body and nucleolus (FIG. 11C), it is evident that SLIM provides optical sectioning (FIGS. 11D-11E). The z-axis elongation is due to the details of the image formation in our microscope, i.e. its three-dimensional point spread function. In accordance with further embodiments of the invention, solution of the scattering inverse problem may result in the removal or artifacts and the quantitative three-dimensional distribution of the cell's refractive index.

SLIM dynamic imaging of live cells has been demonstrated over various time scales, from 0.4 s to more than 1 day. FIGS. 12A-12H summarize the dynamic measurements obtained via 397 SLIM images of a mixed glial-microglial cell culture over a period of 13 minutes. Microglia are immunologically competent cells in the brain that exist in different morphological and functional states in the central nervous system, from beneficial to destructive. Through nutrient deprivation, hypothalamic mixed glial cultures exhibit rapid microglial proliferation accompanied by the emergence of reactive microglia. These macrophages exhibit dynamic migratory, probing, phagocytic behaviors.

Figure 12F:
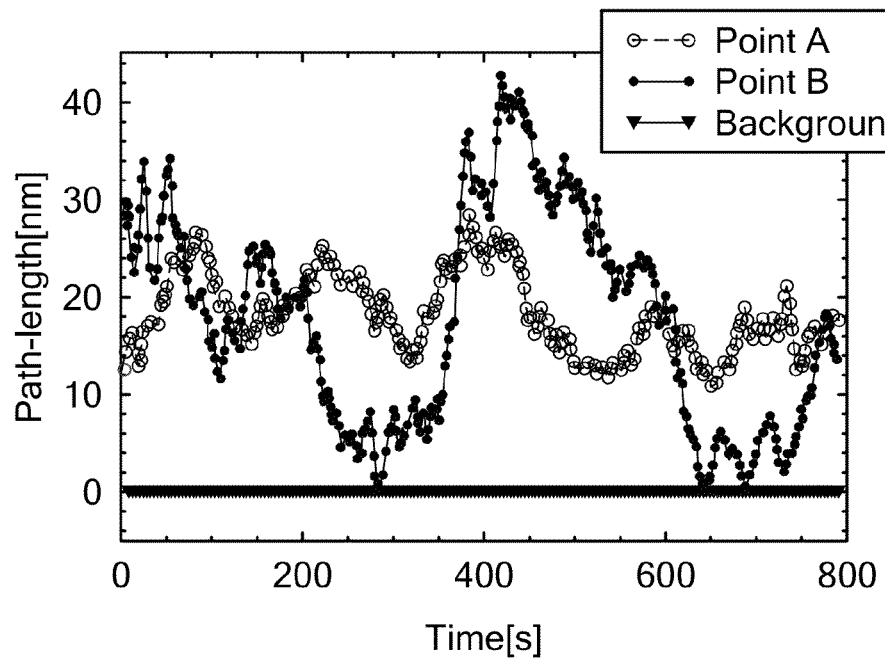

Glial cells and the neighboring reactive microglia were analyzed for dynamics as reported by the fluctuations in the optical path-length. In order to illustrate the microglia dynamics, we numerically suppressed the translation motion via an algorithm implemented in ImageJ and described by Thevanaz et al., in *IEEE Trans. Image Processing*, vol. 7, p. 27 (1998), which is incorporated herein by reference. Phase contrast (PC) results are also shown for comparison in FIGS. 12B and 12C. PC cannot provide quantitative information about dynamic changes in optical path-length, because the intensity is not linearly dependent on phase. In addition, the cell size is significantly overestimated by PC due to the well known halo artifact, which makes the borders of the cell appear bright, as evident, insofar as FIGS. 12B and 12D show the same field of view. By contrast, SLIM reveals details of intracellular dynamics, as evidenced by the time-traces (FIG. 12E). Path-length fluctuations associated with two arbitrary points on the cell reveal interesting, quasi-periodic behavior (FIG. 12F). The rhythmic motions have different periods at different sites on the cell, which may indicate metabolic activity of different rates. This periodicity can be observed as the cell extends broad, dynamic filopodial ruffles under, and above, the neighboring glial cells.

Figure 12G:
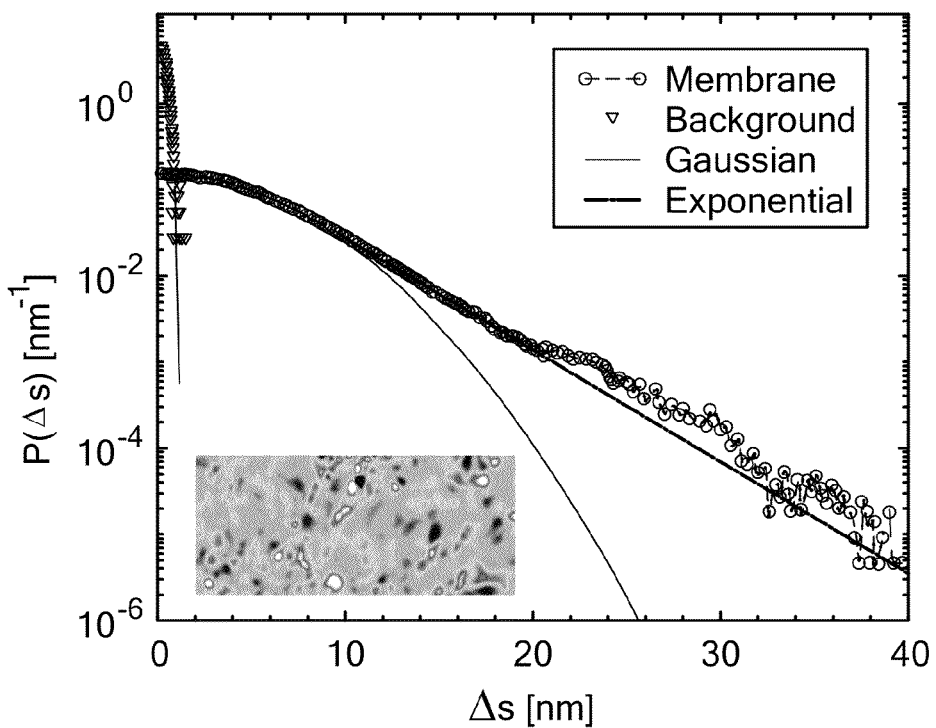
Figure 12H:
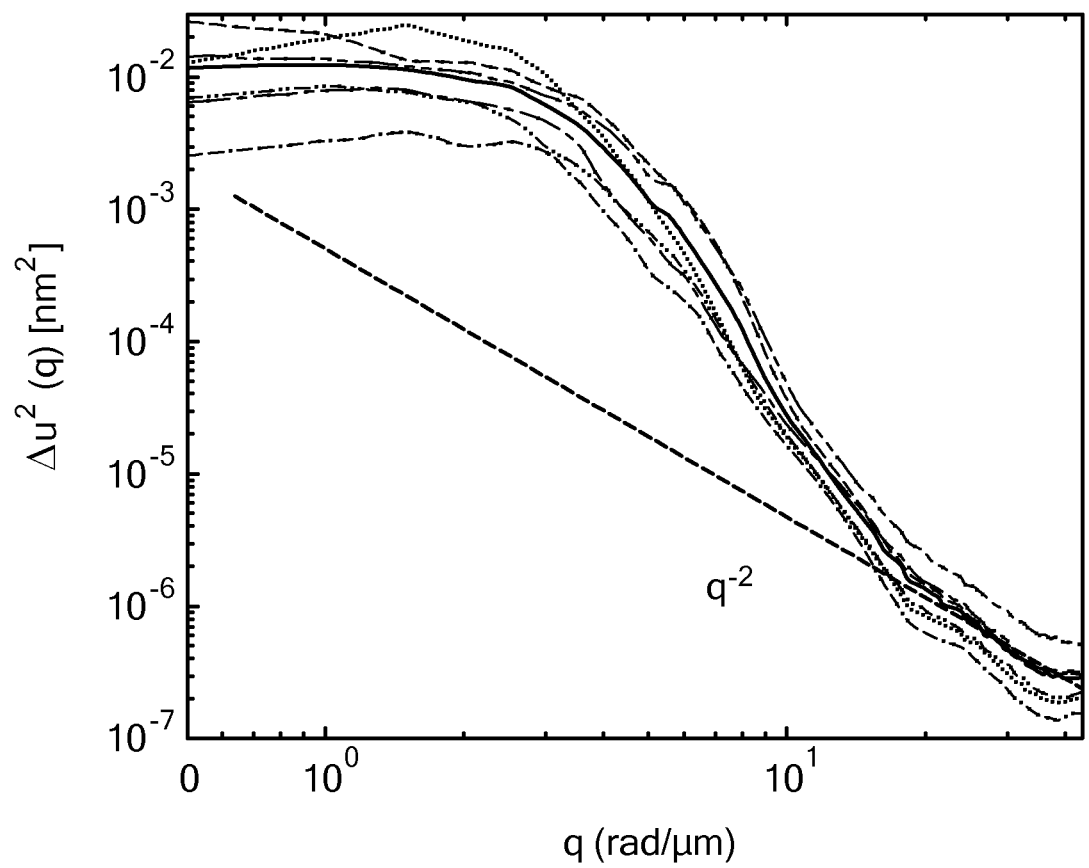

Fluctuations of a membrane patch on the glial cell received further study. Due to the extremely low noise level of SLIM, the probability distribution of path-length displacements between two successive frames was retrieved with a dynamic range of over 5 orders of magnitude, as shown in FIG. 12G). Note that these optical path-length fluctuations Δs are due to both membrane displacements Δu and local refractive index changes due to cytoskeleton dynamics. Remarkably, this distribution can be fitted very well with a Gaussian function up to path-length displacements Δs=10 nm, at which point the curve crosses over to an exponential decay. The normal distribution suggests that the small amplitude fluctuations are the result of numerous uncorrelated processes governed by equilibrium. These fluctuations might be attributable to membrane Brownian motion. The larger (>10 nm) amplitudes characterized by longer tails are indicative of deterministic phenomena, which relate to metabolic activity captured via refractive index fluctuations. In order to confirm the hypothesis that the Gaussian fluctuations are due to membrane motions, we performed the spatial wave vector decomposition of the mean squared displacements, $\Delta u^2 = \Delta s^2/\overline{\Delta n}^2$, with $\overline{\Delta n}=0.047$ the average refractive index difference between the cytosol and culture medium (24). Remarkably, it was found that at small displacements, i.e. large q's, the curve transitions to a $q^{-2}$ dependence, which is a signature of tension-dominated motions in a membrane, as depicted in FIG. 12H. This behavior indicates that the small (high spatial frequency) "ripples" in our measurement correspond to the Gaussian fluctuations, which makes the dynamics problem similar to that of the red blood cell membrane fluctuations. Assuming that these motions are due to the thermal fluctuations of the membrane, we extracted the tension coefficient σ by fitting the data to $\Delta u^2(q)=k_B T/\sigma q^2$. The measured value, $\sigma=(2.5\pm1.1)\cdot10^{-5}$ N/m, shows that the tension in glial cell membranes is approximately an order of magnitude higher than in normal red blood cells, which are known to be significantly softer than eukaryotic cells. Our values are compatible with the $\sigma=3\cdot10^{-5}$ N/m previously measured on neutrophils by micropipette aspiration, although, compared to micropipette aspiration, SLIM has the distinct advantages of being non-contact and providing spatially-resolved information within one cell or across many cells.

With the high resolution demonstrated by embodiments of the invention as heretofore described, dynamic quantitative phase contrast imaging also becomes possible. One advantageous application is that of studying neuron transportation. While current frame rates of ~5 Hz are limited by operation of the SLM, that is not a fundamental limitation of the techniques described and claimed herein.

Advantageous applications of the methods and apparatus described herein include quantifying nanoscale motions in live cells and measuring membrane tension without physical contact, quantifying cell growth non-invasively, performing nanoscale profilometry of thin films in reflection and transmission, and measuring refractive index of cylindrical objects such as nanotubes and neuron processors. Additionally, elastic scattering properties of both single cells and tissues may be measured, and may the dynamic scattering properties, again, of both single cells and tissues.

FTLS for Quantifying Optical Properties of Organ Tissue

The apparatus and methods heretofore described may be used advantageously to extract optical scattering properties of tissue. More particularly, the scattering mean free path $l_s$ and anisotropy factor g, may be measured in tissue slices of different organs. This direct measurement of tissue scattering parameters allows predicting the wave transport phenomena within the organ of interest at a multitude of scales.

Figure 13A:
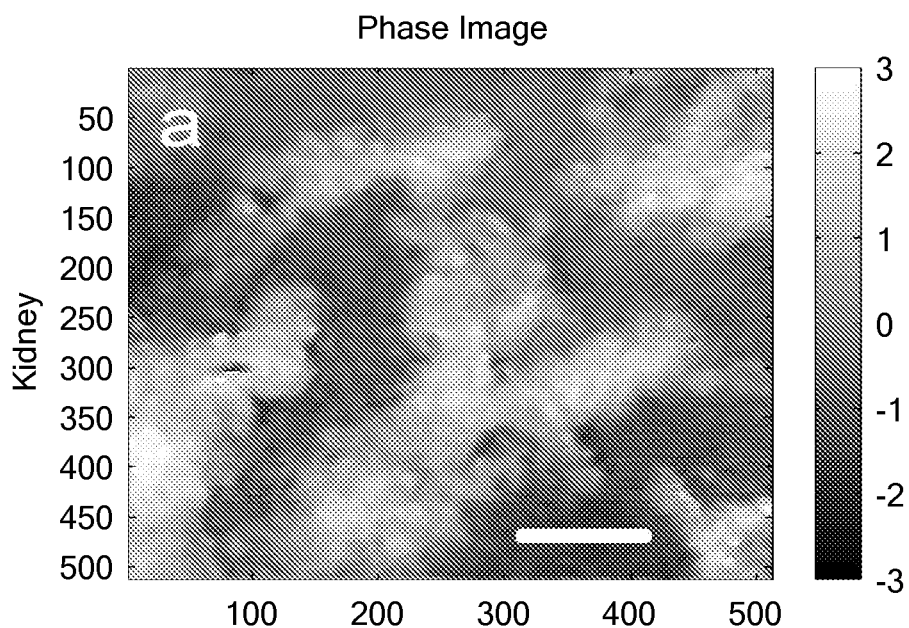
FIGS. 13a-13c are quantitative phase images (512×512 pixels) for rat kidney, liver and brain, respectively, relative to a scale bar of 25 μm.
Figure 13B:
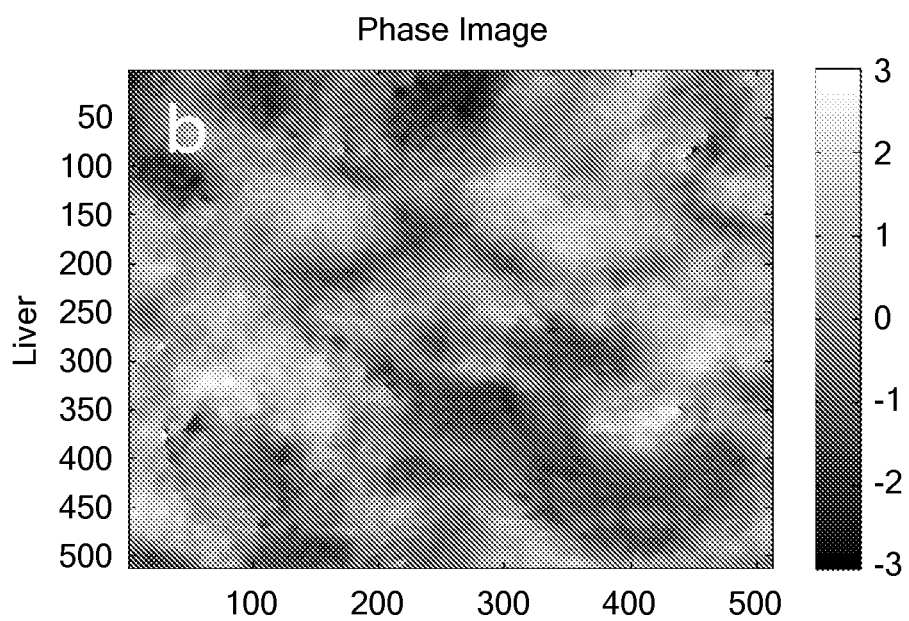
Figure 13C:
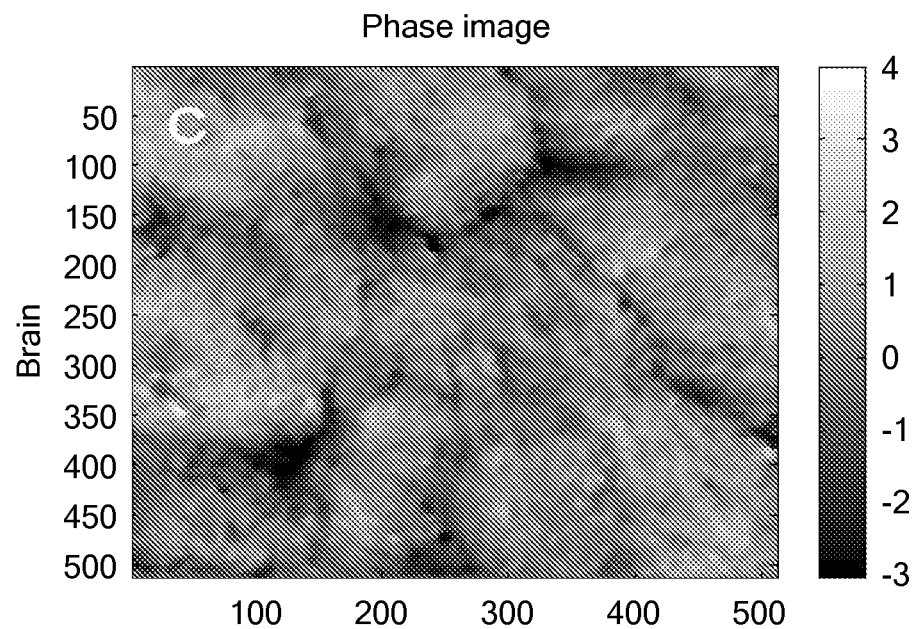
Figure 13D:
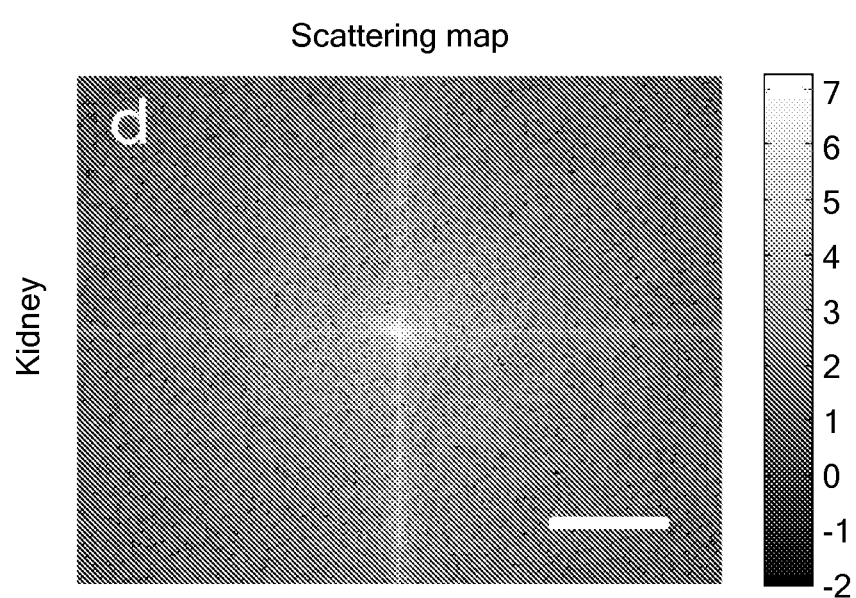
FIGS. 13d-13f are scattering maps (logarithmic scale) associated with the phase images of FIGS. 13a-13c.
Figure 13E:
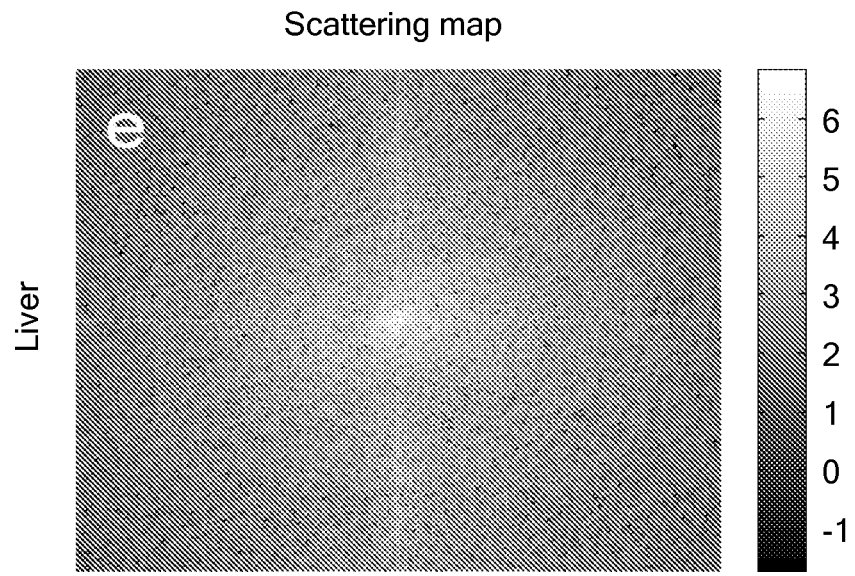
Figure 13F:
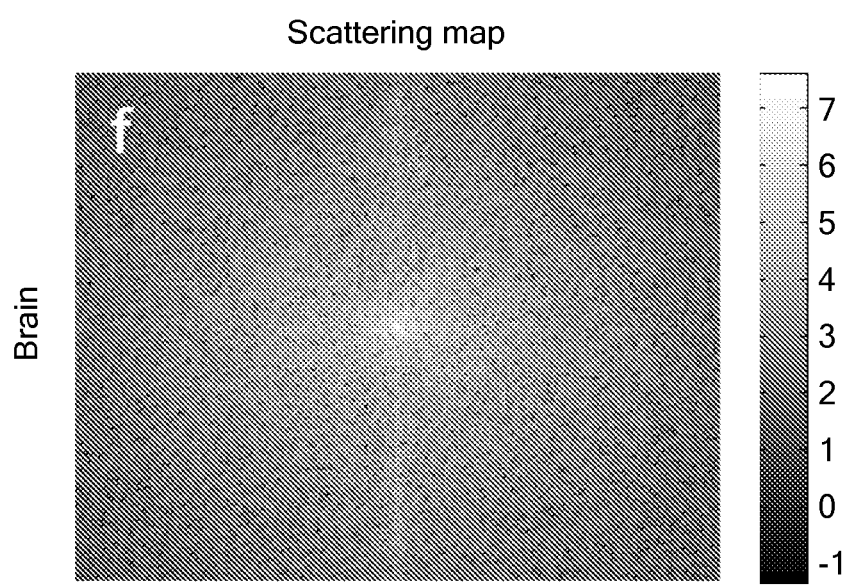

FIGS. 13a-c show examples of quantitative phase images associated with 5-micron tissue slices for three different organs from a rat. The scattered intensity for each slice is obtained by Fourier transforming the complex image field, $$\tilde{I}(q) \propto |\iint (|U(r)| e^{i\phi(r)}) e^{iq \cdot r} d^2 r|^2, \quad (38)$$

where q is the momentum transfer, of modulus $|q|=(4\pi/\lambda)\sin(\theta/2)$, with $\theta$ the scattering angle. The scattering maps associated with the phase images 13a-c are shown in FIGS. 13d-f.

Figure 14A:
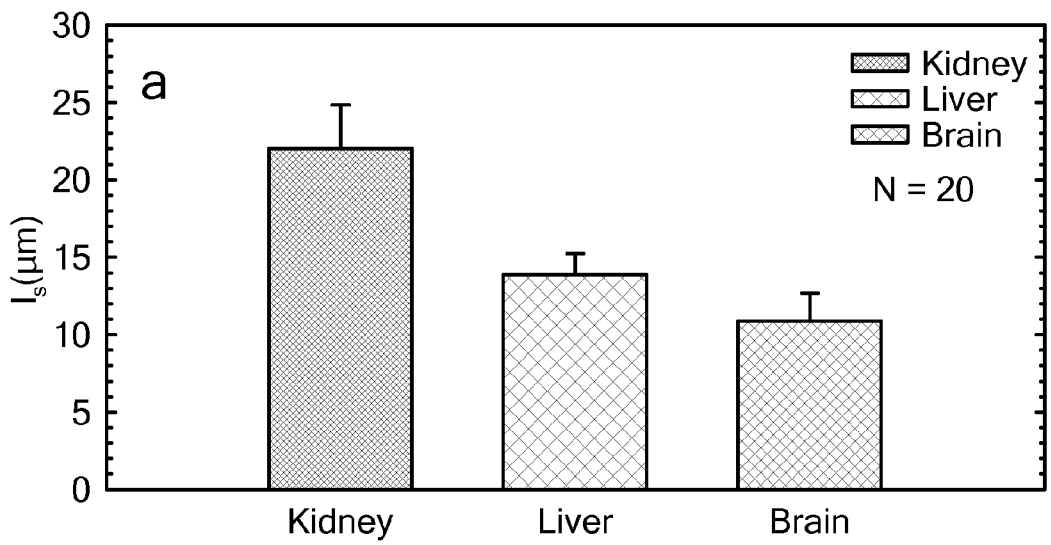
FIGS. 14a-14c, respectively, depict FTLS measurements of the scattering mean free path $l_s$, anisotropy factors and transport mean free path for the three rat organs with 20 samples per group.

The scattering mean free path $l_s$ may be measured by quantifying the attenuation due to scattering for each slice via the Lambert-Beer law, $l_s = -d/\ln[I(d)/I_0]$, where d is the thickness of the tissue, I(d) is the irradiance of the unscattered light after transmission through the tissue, and $I_0$ is the total irradiance, i.e., the sum of the scattered and unscattered components. The unscattered intensity I(d), i.e., the spatial DC component, is evaluated by integrating the angular scattering over the diffraction spot around the origin. The resulting $l_s$ values for 20 samples for each organ, from the same rat are summarized in FIG. 14a.

The anisotropy factor g is defined as the average cosine of the scattering angle, $$g = \frac{\int_{-1}^{1} \cos(\theta) p[\cos(\theta)] d[\cos(\theta)]}{\int_{-1}^{1} p[\cos(\theta)] d[\cos(\theta)]}, \quad (39)$$

where p is the normalized angular scattering, i.e., the phase function. Note that, since Eq. 38 applies to tissue slices of thickness $d < l_s$, it cannot be used directly in Eq. 39 to extract g since g values in this case will be thickness-dependent. This is so because the calculation in Eq. 39 is defined over tissue of thickness $d = l_s$, which describes the average scattering properties of the tissue (i.e. independent of how the tissue is cut). Under the weakly scattering regime of interest here, this angular scattering distribution p is obtained by propagating the complex field numerically through $N = l_s/d$ layers of d=5 microns thickness, $$p(q) \propto |\iint [U(r)]^N e^{iq \cdot r} d^2 r|^2. \quad (40)$$

Eq. 40 applies to a slice of thickness $l_s$. It reflects that, by propagating through N weakly scattering layers of tissue, the total phase accumulation is the sum of the phase shifts from each layer, as is typically assumed in phase imaging of transparent structures. In essence, Eq. 38 describes the tissue slice angular scattering, while Eq. 40 characterizes the bulk tissue. The angular scattering distribution, or phase function, $p(\theta)$ is obtained by performing azimuthal averaging of the scattering map, p(q), associated with each tissue sample (FIG. 13a-c). The maximum scattering angle was determined by the numeric aperture of the objective lens, and it is typically about 18°. The angular scattering data were further fitted with Gegenbauer Kernel (GK) phase function, as described in Reynolds et al., *Approximate 2-Parameter Phase Function for Light-Scattering*, Journal of the Optical Society of America, 70, pp. 1206-12, (1980).

$$P(\theta) = ag \cdot \frac{(1-g^2)^{2a}}{\pi[1+g^2-2g\cos(\theta)]^{(a+1)}[(1+g)^{2a}-(1-g)^{2a}]} \quad (41)$$

Figure 14B:
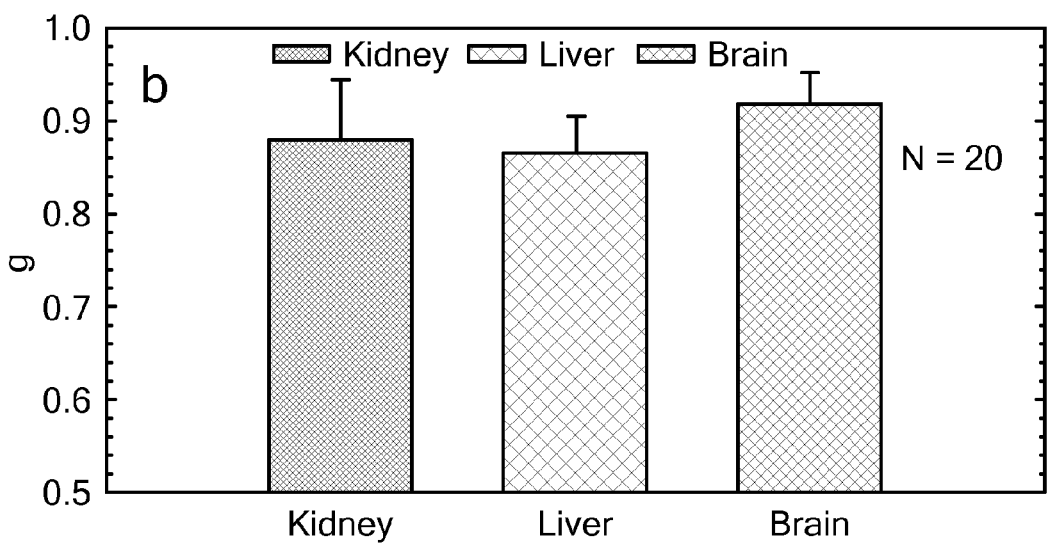
Figure 14C:
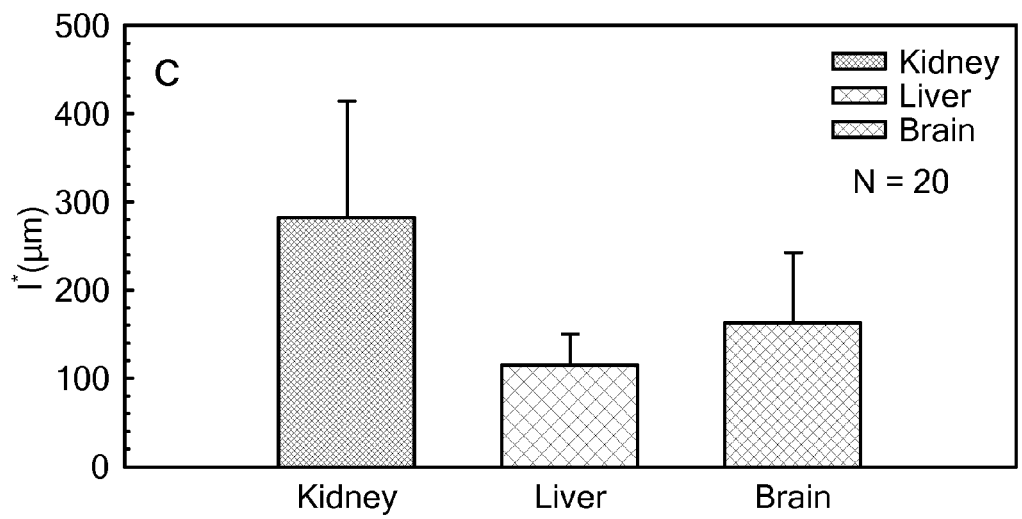
Figure 14D:
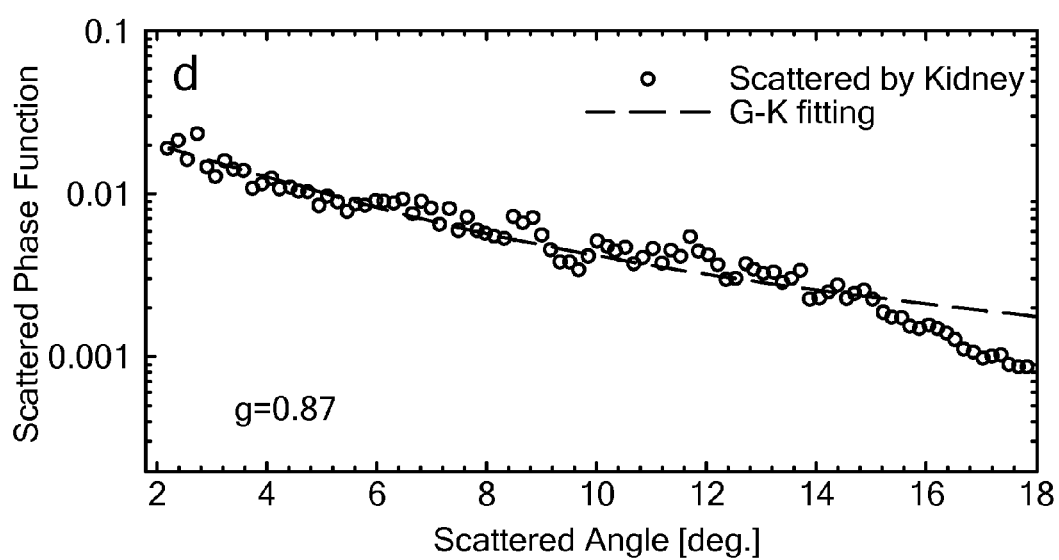
FIGS. 14d-14f are angular scattering plots associated with the scattering maps in FIGS. 14a-14c. The dash lines indicate fits with a Gegenbauer Kernel phase function.
Figure 14E:
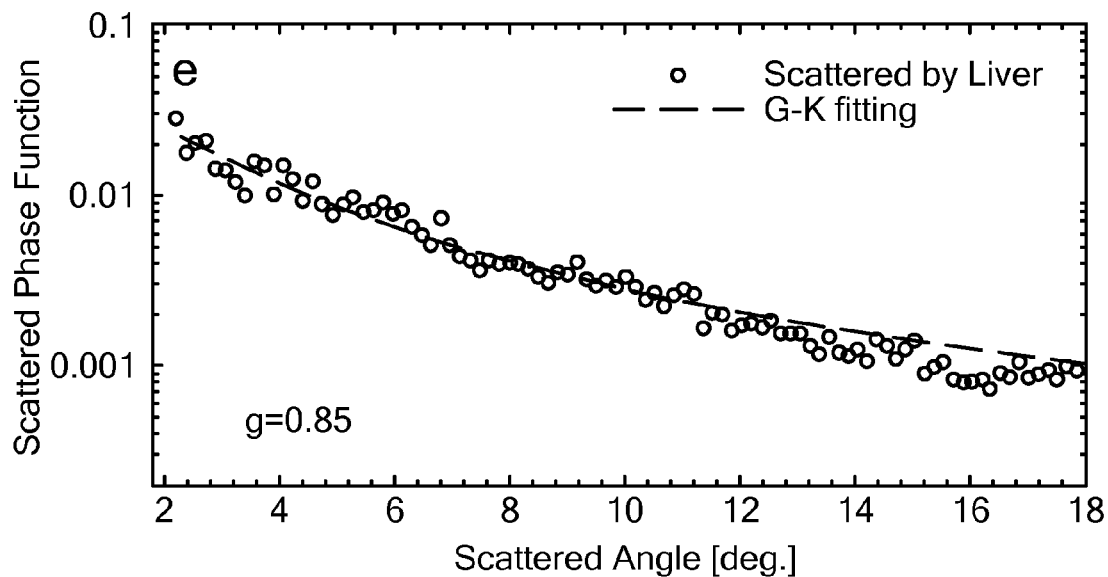
Figure 14F:
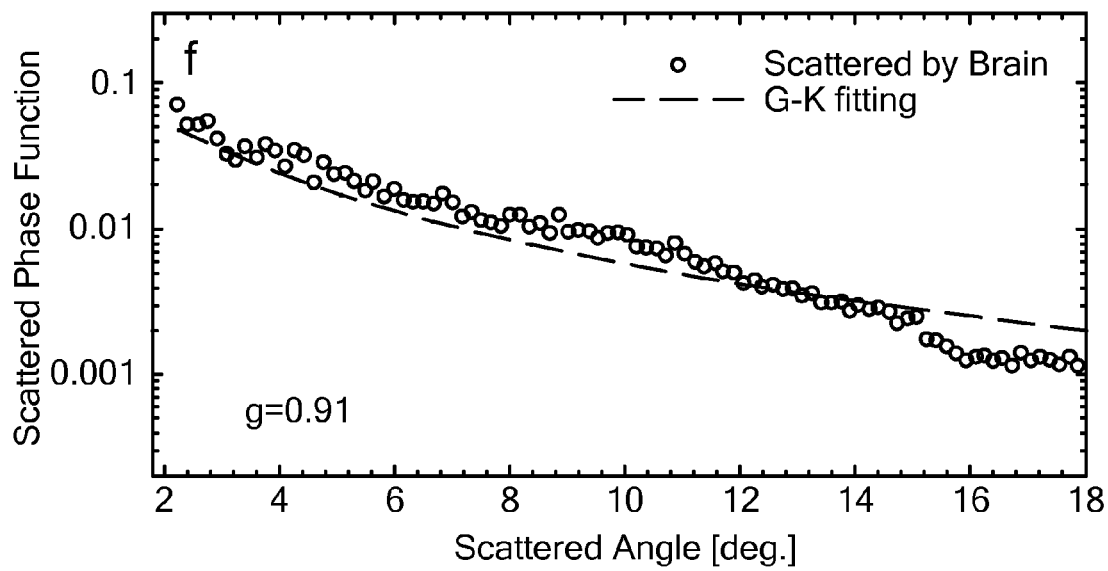

Note that g can be estimated directly from the angular scattering data via its definition in Eq. 39. However, because of the limited angular range measured, g tends to be overestimated by this method, and, thus, the GK fit offers a more reliable alternative than the widely used Henyey-Greenstein (HG) phase function with the parameter a=1/2. The representative fitting plots for each sample are shown in FIGS. 14d-f. The final values of g are included in FIG. 14b.

From these measurements of thin, singly scattering slices, the behavior of light transport in thick, strongly scattering tissue may be estimated. Thus the transport mean free path, which is the renormalized scattering length to account for the anisotropic phase function, can be obtained as $l^* = l_s/(1-g)$. The $l^*$ values for 20 samples from each organ are shown in FIG. 14c, which show larger standard deviations compared to $l_s$ and g. These larger fluctuations are due to the combined effect of measuring both g and $l_s$.

Thus, FTLS can quantify the angular scattering properties of thin tissues, which in turn provides the scattering mean free path $l_s$ and anisotropy factor g, for the macroscopic (bulk) organ. Based on the knowledge of ls, g, and l*, one can predict the outcome of a broad range of scattering experiments on large samples (size >>l*), via numerical solutions to the transport equation, or analytical solutions to the diffusion equation.

FTLS measurements of unstained tissue biopsies, which are broadly available, may be used to provide a large scattering database, where various tissue types, healthy and diseased, are fully characterized in terms of their scattering properties.

Scattering Phase Functions of Distinct Cell Types

At the opposite end of the spatial scale from the foregoing example, FTLS may be used in combination with high-resolution microscopes to describe the angular (and dynamic) scattering of subcellular structures. An application to the sorting of cell types is first described, followed by a description of FTLS sensitivity to spatio-temporal organization of actin cytoskeleton.

Figure 15A:
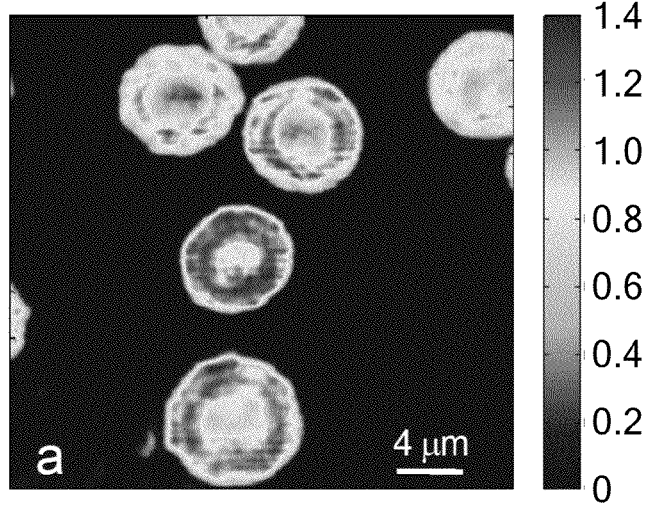
FIGS. 15a-15c are quantitative phase images, respectively, of red blood cells, a C2C12 cell, and a neuron, with the scale bar indicating 4 microns.
Figure 15B:
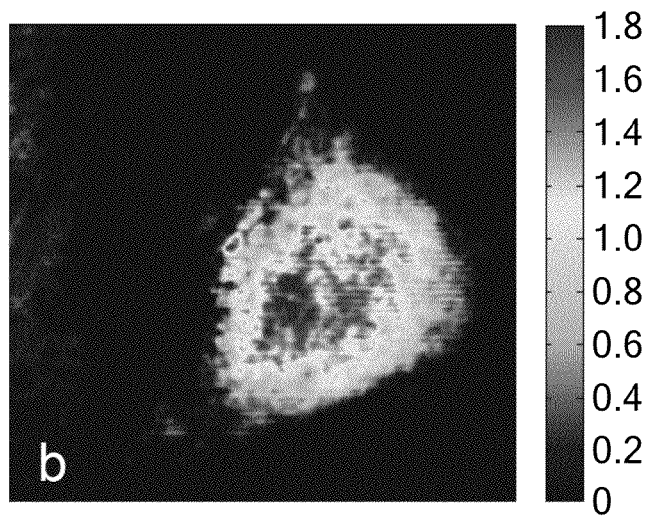
Figure 15C:
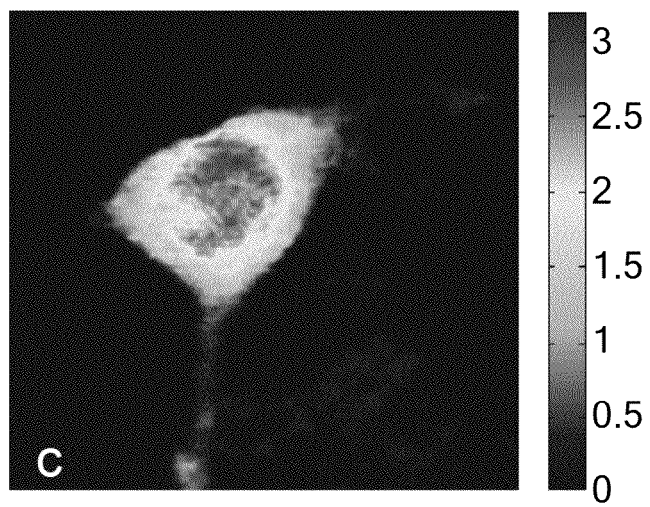

In an example of the use of the apparatus and methods heretofore described to sort cells, red blood cells, myoblasts (C2C12), and neurons were studied. FIGS. 15a-15c show quantitative phase images, respectively, of red blood cells, a myoblast C2C12 cell, and a hippocampal neuron from a rat. FIGS. 15d-f show the angular scattering distributions associated with the same samples. For each group, measurements were performed on different fields of view. FTLS provides these scattering signals over approximately 35 degrees in scattering angle and several decades in intensity. For comparison, the scattering signature of the background (i.e. culture medium with no cells in the field of view by using threshold) is shown, reflecting inhomogeneities, impurities on optics, and residues in the culture medium. These measurements demonstrate that FTLS is sensitive to the scattering signals from single cells, thus providing an advantage over measurements on suspensions, where subtle details of the cell structures may be washed out because signals are averaged over various cell orientations. Such a feature is present in FIG. 15d, where significant peaks are measured from red blood cells (diameter 7.44±0.34 μm) at around 5.5° and 7.8° scattering angle. These peaks have been measured repeatedly and they are confirmed by finite difference and time domain simulation by Karlsson et al., (supra).

A statistical algorithm based on principle component analysis (PCA) may be applied, using FTLS data, aimed at maximizing the differences among the cell groups and providing an automatic means for cell sorting. PCA is described in Jolliffe, *Principal Component analysis* (2d ed.) (2006), which is incorporated herein by reference. PCA identifies patterns in high dimensional data sets by retaining those characteristics of the data set that contribute most to its variance. In the analysis that was performed, the n (n=1 ... 45) measurements for the 3 cell types (15 measurements per group) were averaged to obtain the average scattered intensity, $$\overline{I(\theta_m)} = \frac{1}{45} \sum_{n=1\ldots 45} I_n(\theta_m),$$

with m=1 ... 35 denoting the number of scattering angles. A matrix $\Delta Y_{nm}$ of variances is generated, where n indexes the different measurements and m the scattering angles. The covariance matrix associated with $\Delta Y$, $Cov(\Delta Y)$, is calculated and its eigenvalues and eigenvectors extracted. The three principal components are obtained by retaining three eigenvectors corresponding to the largest eigenvalues. In order to build the training set, 45 measurements (i.e., 15 per cell type) were taken and processed following the procedure described above. Additional measurements for each sample were taken and mixed with the results used for the training sets to test for the accuracy of our cell differentiation.

Figure 16A:
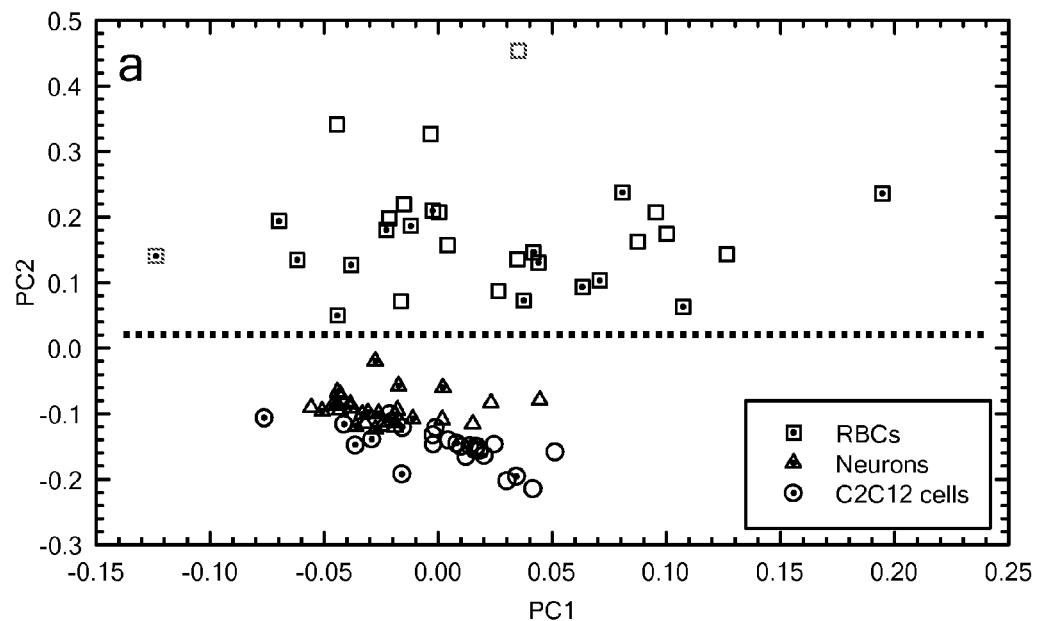
FIGS. 16a and 16b plot principle component analyses of the experimental data for the three cell types, as indicated.
Figure 16B:
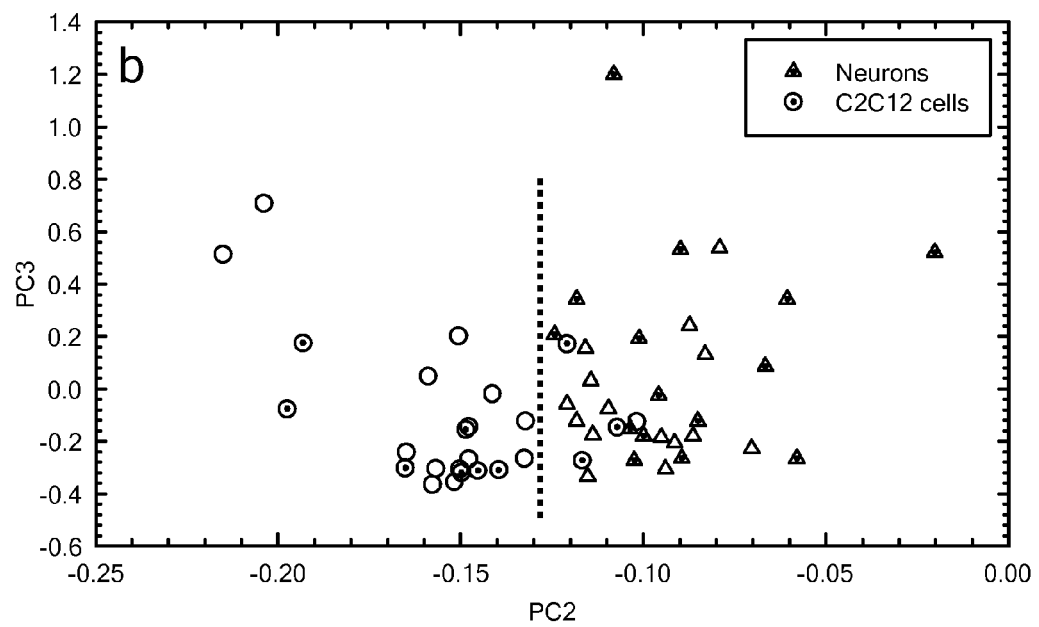

FIGS. 16a and 16b shows a representation of the data where each point in the plot is associated with a particular FTLS measurement (15 measurements per group for the training sets; and another additional 15 measurements per group for neurons and RBCs and 10 for C2C12 cells for the testing sets). Thus, individual points in FIG. 16a-b have as coordinates the dot product between the corresponding data set and each of the 3 PC's. This analysis of our scattering measurement for the three biological samples shows clear separation among the three training sets (symbols with a "+" sign in the middle are the testing measurements for each sample). Sensitivity values of 100%, 100% and 70% were obtained, and specificities of 100%, 88% and 100%, for RBCs, neurons and C2C12 cells.

Quantitative phase imaging, in accordance with embodiments of the present invention, may thus be used to differentiate between various cell types. Due to the particular imaging geometry used, scattering phase functions associated with single cells can be retrieved over a broad range of angles. This remarkable sensitivity to weak scattering signals provides for a new generation of cytometry technology, which, in addition to the intensity information, extracts the structural details encoded in the phase of the optical field. FTLS may advantageously improve flow cytometry in that it operates without the need for exogenous tags. A microchannel platform provides a high-throughput combination of flow cytometry and imaging. A flow cytometer applying FTLS has a flow cell for streaming biological cells within a fluid medium, a source of substantially spatially coherent illumination for illuminating a subset of the biological cells within the flow cell, an objective for collecting light scattered by the illuminated subset of biological cells and for imaging the light in an imaging plane. A dispersing element diffracts light in an imaging plane into at least two diffraction orders, one order comprising a reference beam, with a spatial filtering lens system provided for removing any spatial structure due to the fluid medium from the reference beam. A detector array is used to create an interference signal based on combination of the two diffraction orders, with a processor transforming the interference signal to obtain an angular scattering distribution in a scattering plane associated with the illuminated subset of biological cells. This allows the cells to be characterized on the basis of angular scattering distribution.

Dynamic Scattering Properties of Live Cells Over Time Scales of Seconds to Hours The apparatus and methods heretofore described may be used advantageously to study slow active dynamics such as that of glial cytoskeleton. Enteric glial cells (EGC) of the enteric (i.e. intestinal) nervous system have long been considered a mechanical support. However, more recent findings provide insight to more complex homeostatic and inflammatory interactions with neurons, lymphocytes, epithelial cells and capillaries of the gut to modulate gastrointestinal motility and respond to inflammation.

During the FTLS measurement, the EGC cells were maintained under constant temperature at 37° C. The sensitivity of FTLS to actin dynamics was tested by controlling its polymerization activity. In order to inhibit actin polymerization, Cytochalasin-D (Cyto-D), approximately 5 µM in Hibernate-A, was added to the sample dishes. Cyto-D is a naturally occurring fungal metabolite known to have potent inhibitory action on actin filaments by capping and preventing filament polymerization and depolymerization at the rapidly elongating end of the filament. By capping this "barbed" end, the increased dissociation at the pointed end continues to shorten the actin filament. In this way, Cyto-D alters cytoskeleton and membrane dynamics which was captured via our FTLS measurement.

Figure 17C:
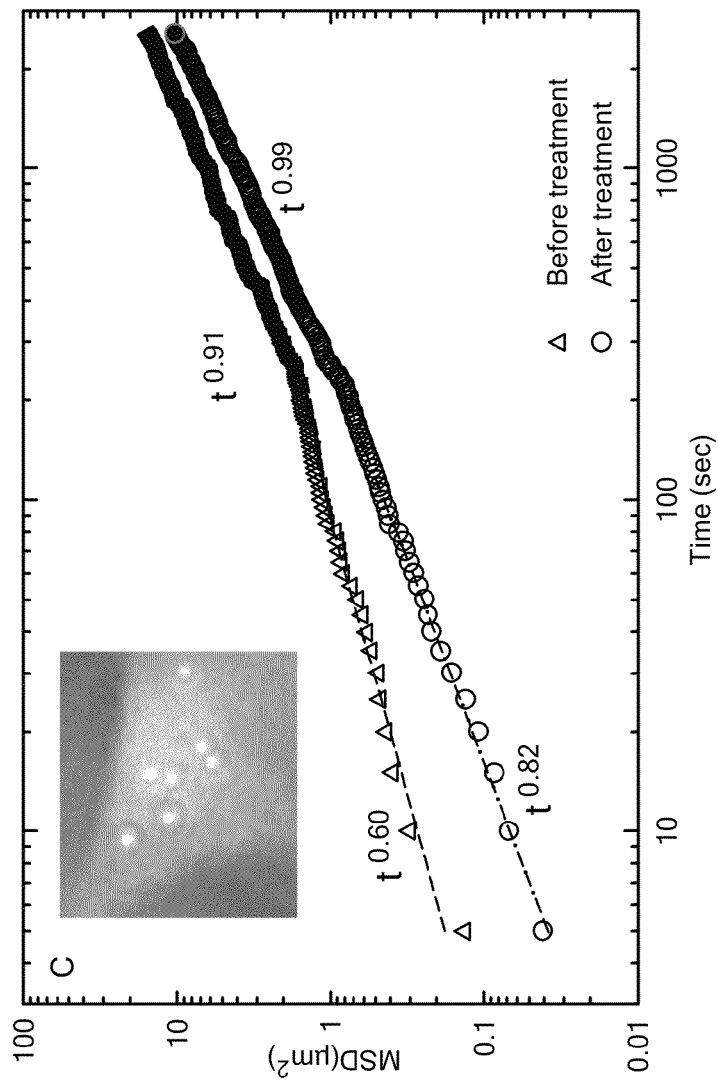
FIG. 17c summarizes the mean-squared bead displacement of FIGS. 17a and 17b as a function of time.
Figure 17A:
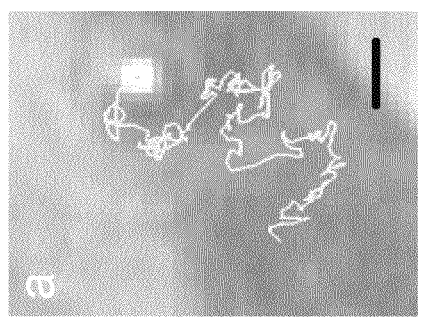
FIGS. 17a and 17b present qualitative trajectories of a bead attached to an actin cell, without, and with, respectively, the presence of Cyto-D inhibitor.
Figure 17B:
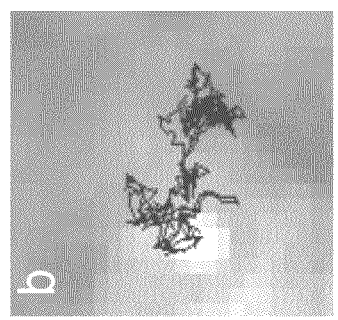

One feature of the present invention is its ability to render simultaneously angular scattering from an entire range of angles, limited only by the numerical aperture of the microscope objective. FIG. 17c shows the power spectrum of the fluctuations for the same cell (shown in FIGS. 17a and 17b) before and after the actin inhibition, as function of both frequency and modulus of the wave vector q. There is a significant difference between the two spatio-temporal power spectra as can be qualitatively observed in FIG. 17c. Thus, after actin inhibition, the functional dependence of P(f) does not change notably with varying q, which contrasts with the situation where the cell cytoskeleton is intact. Therefore, disrupting the actin cytoskeleton, provides a new way of studying the cell membrane dynamics at thermal equilibrium.

The embodiments of the invention heretofore described are intended to be merely exemplary and numerous variations and modifications will be apparent to those skilled in the art. All such variations and modifications are intended to be within the scope of the present invention as defined in any appended claims.

What is claimed is:

1. A method for determining an angular scattering distribution, in a scattering plane, of at least one particle, the method comprising:
   a. illuminating a sample containing the at least one particle with light;
   b. obtaining a single interference image comprising an interference signal by combining, at a detector array disposed at an image plane,
      a first instance of the light, the first instance substantially devoid of spatial frequency information due to the sample,
      with a second instance of the light, the second instance containing spatial frequency information due to scattering by the sample,
      such as to produce the interference signal;
   c. numerically propagating a pattern associated with the interference signal of the single interference image at the image plane to obtain the angular scattering distribution in the scattering plane; and
   d. providing a tangible image of the angular scattering distribution in the scattering plane.

2. A method in accordance with claim 1, further comprising:
   spatially high-pass filtering the interference signal to obtain an interferogram based on cross-term of the first and second instances of the light.

3. A method in accordance with claim 1, wherein the first instance of the light does not traverse the sample.

4. A method in accordance with claim 1, wherein the first and second instances of the light both traverse the sample and are split, into a zeroeth order and at least one higher order, with respect to one another by a diffractive element disposed substantially in an image plane.

5. A method in accordance with claim 4, wherein the first instance of the light is derived from the zeroeth order of the diffractive element.

6. A method in accordance with claim 1, wherein the first instance of the light is low-pass filtered in a Fourier plane of a spatial filtering lens system.

7. A method in accordance with claim 1, further comprising a step of separating the angular scattering distribution into a form field characterizing a single particle and a structural field describing spatial correlations in particle positions.

8. A method in accordance with claim 1, further comprising repeating steps (a)-(d) for obtaining a set of dynamic light scattering signals.

9. A method in accordance with claim 8, further comprising obtaining a power spectrum of the set of dynamic light scattering signals.

10. The method of claim 1, wherein the sample comprises the particle provided in a flowing fluid medium.

11. The method of claim 10, wherein the particle is a biological cell.

12. The method of claim 1, further comprising providing the sample by streaming biological cells within a fluid medium.

13. The method of claim 1, wherein the sample is provided in a flow cytometer.

14. The method of claim 1, wherein the sample comprises a cell, tissue or thin film.

15. The method of claim 14, providing a noninvasive and noncontact means of characterizing the cell, tissue or thin film.

16. A flow cytometer comprising:
   a. a flow cell for streaming biological cells within a fluid medium;
   b. a source of substantially spatially coherent illumination for illuminating a subset of the biological cells within the flow cell;
   c. an objective for collecting light scattered by the illuminated subset of biological cells and for imaging the light in an imaging plane;
   d. a dispersing element for diffracting the light in the imaging plane into at least two diffraction orders, one order comprising a reference beam;
   e. a spatial filtering lens system for removing any spatial structure due to the fluid medium from the reference beam;
   f. a detector array disposed at a sample image plane for creating a single interference image comprising an interference signal based on combination of the two diffraction orders; and
   g. a processor for transforming the interference signal by numerically propagating a pattern associated with the interference signal of the single interference image to obtain an angular scattering distribution in a scattering plane associated with the illuminated subset of biological cells and for characterizing the cells based on the angular scattering distribution.

\* \* \* \* \*